(12) United States Patent
Dai et al.

(10) Patent No.: US 8,232,306 B2
(45) Date of Patent: Jul. 31, 2012

(54) METHODS FOR DETECTING SULFHYDRYL-CONTAINING COMPOUNDS IN A BIOLOGICAL TEST SAMPLE

(75) Inventors: Yuqin Dai, Foster City, CA (US);
Donavon McConn, Oakland, CA (US);
Huiyu Zhou, Novato, CA (US)

(73) Assignee: Theravance, Inc., South San Francisco, CA (US)

( * ) Notice: Subject to any disclaimer, the term of this patent is extended or adjusted under 35 U.S.C. 154(b) by 400 days.

(21) Appl. No.: 12/579,612

(22) Filed: Oct. 15, 2009

(65) Prior Publication Data
US 2010/0099134 A1     Apr. 22, 2010

Related U.S. Application Data

(60) Provisional application No. 61/105,869, filed on Oct. 16, 2008.

(51) Int. Cl.
*A61K 31/4166*     (2006.01)
*C07D 233/70*     (2006.01)

(52) U.S. Cl. .................................. 514/398; 548/324.5

(58) Field of Classification Search ............... 548/324.5; 514/398
See application file for complete search history.

(56) References Cited

U.S. PATENT DOCUMENTS

| 2008/0269305 A1 | 10/2008 | Allegretti et al. |
| 2009/0023228 A1 | 1/2009 | Allegretti et al. |

OTHER PUBLICATIONS

Iyer et al., "Metabolism of [14C]omapatrilat, a Sulfhydryl-containing Vasopeptidase Inhibitor in Humans", Drug Metabolism and Disposition, vol. 29, No. 1, pp. 60-69 (2001).*
Jemal et al., "Quantitative determination of BMS186716, a thiol compound, in dog plasma by high-performance liquid chromatography-positive ion electrospray mass spectrometry after formation of the methyl acrylate adduct", Journal of Chromatography B, 693, pp. 109-116 (1997).
Jemal et al., "Quantitative determination of BMS-186716, a thiol compound, in rat plasma by high-performance liquid chromatography-positive ion electrospray mass spectrometry after hydrolysis of the methyl acrylate adduct by the native esterases", Journal of Chromatography B, 698, pp. 123-132 (1997).
Jemal et al., "LC/MS/MS Determination of omapatrilat, a sulfhydryl-containing vasopeptidase inhibitor, and its sulfhydryl- and thioether-containing metabolites in human plasma", Analytical Chemistry, 73, pp. 5450-5456 (2001).
Liu et al., "Determination of total tiopronin in human plasma by LC-ESI-MS using tris(2-carboxy-ethyl)phosphine as reducing reagent and methyl acrylate as derivatization reagent for the thiol group", Journal of Chromatography B, 844, pp. 153-157 (2006).
Srinivas et al., "Bioanalytical considerations for compounds containing free sulfhydryl groups", Biomedical Chromatography, 17, pp. 285-291 (2003).
PCT Notification of Transmittal of the International Search Report and the Written Opinion of the International Searching Authority, or the Declaration of PCT/US2009/060773.

* cited by examiner

*Primary Examiner* — Kamal Saeed
*Assistant Examiner* — Janet L Coppins
(74) *Attorney, Agent, or Firm* — Jeffrey A. Hagenah; Shelley Eberle

(57) ABSTRACT

The invention relates to methods for detecting the presence of a compound of formula I in a biological test sample:

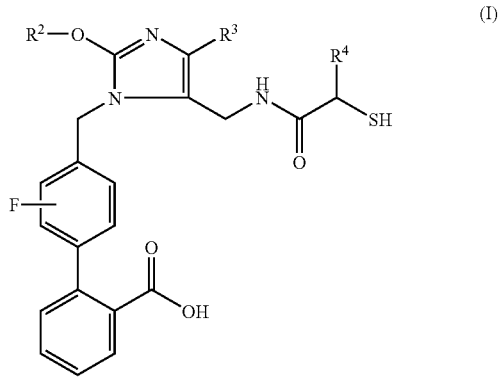

where $R^2$, $R^3$, and $R^4$ are as defined in the specification; or a salt thereof.

5 Claims, 4 Drawing Sheets

METHODS FOR DETECTING SULFHYDRYL-CONTAINING COMPOUNDS IN A BIOLOGICAL TEST SAMPLE

CROSS-REFERENCE TO RELATED APPLICATIONS

This application claims the benefit of U.S. Provisional Application No. 61/105,869, filed on Oct. 16, 2008; the entire disclosure of which is incorporated herein by reference in its entirety.

BACKGROUND OF THE INVENTION

1. Field of the Invention

The present invention relates to methods for detecting the presence of certain sulfhydryl-containing compounds in a biological test sample by either forming a derivative of the sulfhydryl-containing compound or by stabilizing the sulfhydryl-containing compound. This invention also relates to novel derivatives of the sulfhydryl-containing compounds.

2. State of the Art

Commonly-assigned U.S. Publication Nos. 2008/0269305 and 2009/0023228, both to Allegretti et al. filed on Apr. 23, 2008, disclose novel imidazole compounds that are useful as hypertensive agents, the disclosures of which are incorporated herein by reference. In particular, the following sulfhydryl-containing compounds are specifically disclosed in these applications:

4'-{4-ethyl-5-[((S)-2-mercapto-4-methylpentanoylamino)methyl]-2-propoxyimidazol-1-ylmethyl}-3'-fluorobiphenyl-2-carboxylic acid;

4'-{4-ethyl-5-[((S)-2-mercapto-4-methylpentanoylamino)methyl]-2-propoxyimidazol-1-ylmethyl}-2'-fluorobiphenyl-2-carboxylic acid;

4'-{2-ethoxy-4-ethyl-5-[((S)-2-mercapto-4-methylpentanoylamino)methyl]-imidazol-1-ylmethyl}-3'-fluorobiphenyl-2-carboxylic acid; and 4'-{4-cyclopropyl-2-ethoxy-5-[((S)-2-mercapto-4-methylpentanoylamino)-methyl]imidazol-1-ylmethyl}-3'-fluorobiphenyl-2-carboxylic acid.

For many reasons, it is often necessary or desirable to detect or accurately measure the amount of a compound, such as a therapeutic agent, in a biological test sample, such as blood or plasma. However, compounds that contain a sulfhydryl (—SH) group, such as those identified above, can be difficult to detect or measure accurately since the sulfhydryl group may be reactive under certain conditions. For example, in plasma samples, the sulfhydryl group can readily oxidize to form disulfide (—S—S—) containing homodimers or it can form heterodimers with other sulfhydryl groups present in circulating proteins found in plasma (for example, serum albumin, glutathione, and cysteine). In either case, the parent sulfhydryl-containing compound can be difficult to detect and, in particular, the amount or concentration of the parent sulfhydryl-containing compound in the sample can be difficult to measure accurately.

SUMMARY OF THE INVENTION

The present invention provides novel methods for detecting the presence of certain sulfhydryl-containing compounds in a biological test sample, or for measuring the amount of such sulfhydryl-containing compounds in the sample. In one aspect, this invention relates to a method of forming a stable derivative of the sulfhydryl-containing compound and then detecting or measuring the resulting derivatized thiol compound. This aspect of the invention also relates to the novel derivatized thiol compounds. In another aspect, this invention relates to a method of stabilizing the sulfhydryl-containing compound using a reducing agent and then detecting or measuring the sulfhydryl-containing compound itself.

More specifically, one aspect of the invention relates to a method for detecting the presence of a compound of formula I in a biological test sample:

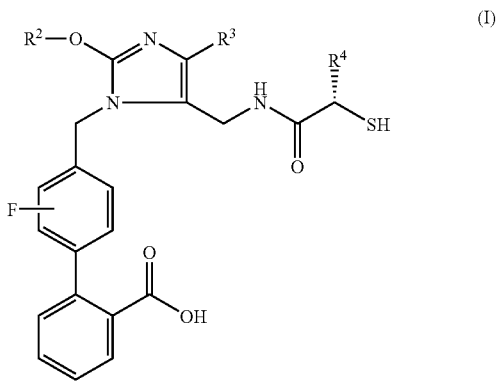

(I)

where: $R^2$ is —$C_{1-10}$alkyl; $R^3$ is —$C_{1-6}$alkyl or —$C_{3-6}$cycloalkyl; and $R^4$ is —$C_{1-6}$alkyl; or a salt thereof; comprising the steps of:

(a) collecting the sample from a mammal;
(b) adding a derivatizing agent to the sample to form a derivatized compound;
(c) subjecting the sample to chromatographic separation; and
(d) detecting the presence of the derivatized compound, and correlating the presence of the derivatized compound to the presence of the compound of formula I.

Another aspect of the invention relates to a compound of formula II:

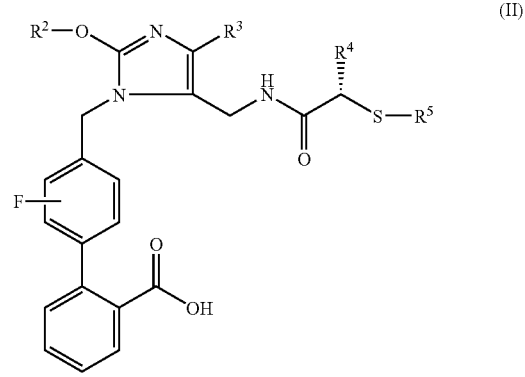

(II)

where: $R^2$ is —$C_{1-10}$alkyl; $R^3$ is —$C_{1-6}$alkyl or —$C_{3-6}$cycloalkyl; $R^4$ is —$C_{1-6}$alkyl; and $R^5$ is —$CH_2CH_2C(O)O$—$C_{1-6}$ alkyl or —$CH_2CH_2C(O)OH$; or a salt thereof. In one embodiment, the derivatized compound in correlating step (d), above, is a compound of formula II.

Still another aspect of the invention relates to a method for detecting the presence of a compound of formula I in a biological test sample, comprising the steps of:

(a) collecting the sample from a mammal;
(b) adding a thiol reducing agent;
(c) subjecting the sample to chromatographic separation; and
(d) detecting the presence of a compound of formula I.

Other aspects and embodiments of the invention are disclosed herein.

BRIEF DESCRIPTION OF THE DRAWINGS

Various aspects of the present invention are illustrated by reference to the accompanying drawings.

DETAILED DESCRIPTION OF THE INVENTION

Definitions

Figure 1:
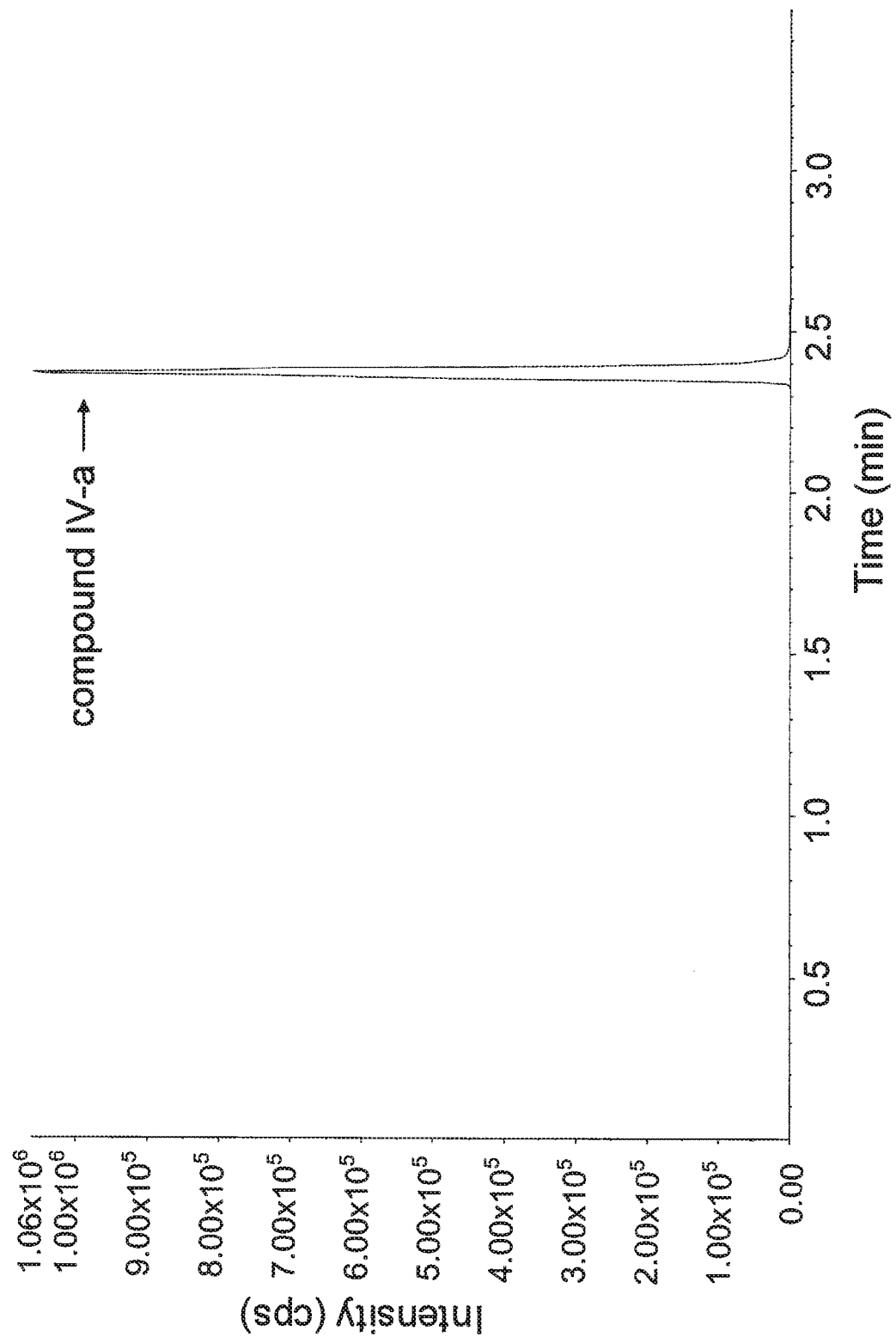
FIG. 1 shows a representative ion chromatogram for the monomer detection method in rat plasma, showing a predominant ion peak of MRM (m/z) 600.2/229.1 at a retention time of 2.38 minutes for compound IV-a.

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements.

The term "salt" is intended to include salts prepared from both organic and inorganic acids and bases. In addition, since the compound of formula I contains both a basic moiety (the imidazole) and an acidic moiety (the carboxylic acid), zwitterions may be formed and are included within the term "salt" as used herein. Salts derived from inorganic bases include ammonium, calcium, copper, ferric, ferrous, lithium, magnesium, manganic, manganous, potassium, sodium, and zinc salts, and the like. Salts derived from organic bases include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. The term "salt" is also intended to include "pharmaceutically acceptable salts," which are salts prepared from bases or acids which are acceptable for administration to a patient, such as a mammal (e.g., salts having acceptable mammalian safety for a given dosage regime). Thus, pharmaceutically acceptable salts can be derived from pharmaceutically acceptable inorganic or organic bases and from pharmaceutically acceptable inorganic or organic acids. However, it is understood that the salts covered by the invention are not required to be pharmaceutically acceptable salts, such as salts of compounds that are not intended for administration to a human.

The term "alkyl" means a monovalent saturated hydrocarbon group which may be linear or branched. Unless otherwise defined, such alkyl groups typically contain from 1 to 10 carbon atoms and include, for example, —$C_{1-4}$alkyl, —$C_{1-6}$alkyl, and —$C_{1-10}$alkyl. Representative alkyl groups include, by way of example, methyl, ethyl, n-propyl, isopropyl, n-butyl, s-butyl, isobutyl, t-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term as subscript. For example, the term "—$C_{1-6}$alkyl" means an alkyl group having from 1 to 6 carbon atoms, and the term "—$C_{3-6}$cycloalkyl" means a cycloalkyl group having from 3 to 6 carbon atoms, where the carbon atoms are in any acceptable configuration.

The term "acrylic acid ester" means an alkyl ester formed by reaction of an alcohol and acrylic acid ($CH_2$=CH(COOH)), and includes compounds such as methyl acrylate, ethyl acrylate, and butyl acrylates such as isobutyl acrylate.

The term "cycloalkyl" means a monovalent saturated carbocyclic hydrocarbon group. Unless otherwise defined, such cycloalkyl groups typically contain from 3 to 10 carbon atoms and include, for example, —$C_{3-5}$cycloalkyl, —$C_{3-6}$cycloalkyl and —$C_{3-7}$cycloalkyl. Representative cycloalkyl groups include, by way of example, cyclopropyl, cyclobutyl, cyclopentyl, cyclohexyl and the like.

All other terms used herein are intended to have their ordinary meaning as understood by those of ordinary skill in the art to which they pertain.

REPRESENTATIVE EMBODIMENTS

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one embodiment, the invention relates to a method for detecting the presence of a compound of formula I:

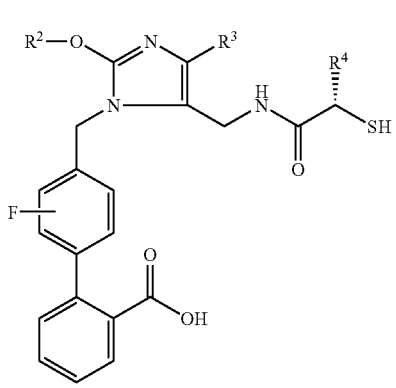

(I)

or a salt thereof, using a reducing agent. Reducing agents such as 1,4-dithiothreitol (DTT) were found to eliminate and/or reverse dimerization of beta-sulfhydryl containing compounds such as:

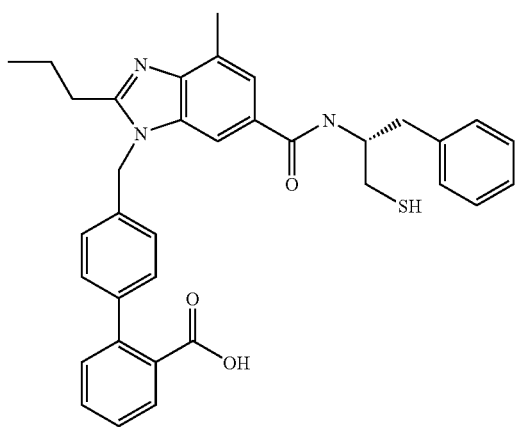

More specifically, beta-sulfhydryl containing compounds were administered to rats, blood samples were collected in 50 mM DTT and centrifuged to obtain plasma, and the plasma samples were then acidified with formic acid. Subsequent analysis indicated that only monomer compounds were present.

Unexpectedly, similar studies conducted with compounds of formula I indicated that both monomer and dimer compounds were present, an indication that the dimers were not completely reduced during blood collection. Additional studies were conducted that used DTT (in the absence of formic acid) or tris(2-carboxyethyl)phosphine (TCEP) as the reducing agent, leading to the discovery that DTT reduction efficiency was pH dependent and decreased significantly in the acidified plasma. The need to find a more efficient method of reducing the sulfhydryl group lead to one embodiment of the present invention, which involves collecting samples with DTT in the absence of formic acid, then further reducing the extracts from plasma samples with TCEP, which tolerates a wider pH range than DTT.

The invention also relates to the derivatized compound, which is a compound of formula II:

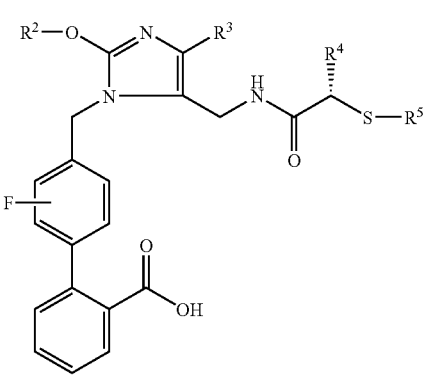

(II)

or a salt thereof.

In compounds of formula I and II, the $R^2$ moiety is $—C_{1-10}$alkyl. In one embodiment, $R^2$ is $—CH_2CH_3$ or $—(CH_2)_2CH_3$. In compounds of formula I and II, the $R^3$ moiety is $—C_{1-6}$alkyl or $—C_{3-6}$cycloalkyl. In one embodiment, $R^3$ is $—C_{1-6}$alkyl, for example, $—CH_2CH_3$. In another embodiment $R^3$ is $—C_{3-6}$cycloalkyl, for example, $R^3$ is cyclopropyl. In compounds of formula I and II, the $R^4$ moiety is $—C_{1-6}$alkyl. In one embodiment, $R^4$ is $—CH_2CH(CH_3)_2$.

In compounds of formula II, the $R^5$ moiety is $—CH_2CH_2C(O)O—C_{1-6}$alkyl or $—CH_2CH_2C(O)OH$. In one embodiment of compounds of formula II, $R^5$ is $—CH_2CH_2C(O)O—C_{1-6}$alkyl. This embodiment can be depicted as formula III:

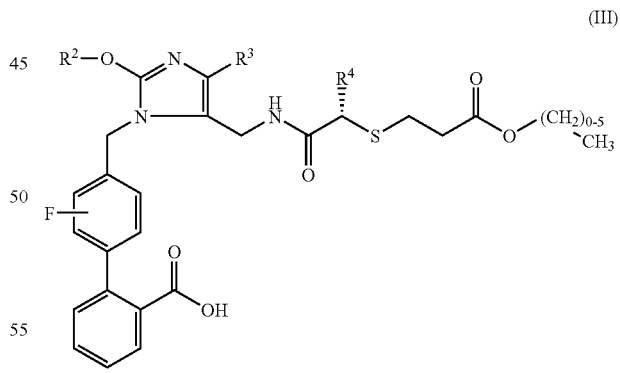

(III)

or a salt thereof. Examples of the $—CH_2CH_2C(O)O—C_{1-6}$alkyl group include, by way of illustration and not limitation, such as $—CH_2CH_2C(O)OCH_3$, $—CH_2CH_2C(O)OCH_2CH_3$, $—CH_2CH_2C(O)O(CH_2)_2CH_3$, $—CH_2CH_2C(O)O(CH_2)_3CH_3$, $—CH_2CH_2C(O)O—CH(CH_3)CH_2CH_3$, $—CH_2CH_2C(O)OCH_2CH(CH_3)_2$, $—CH_2CH_2C(O)OC(CH_3)_3$, and so forth.

In one embodiment of compounds of formula II, $R^5$ is —$CH_2CH_2C(O)OH$. This embodiment can be depicted as formula IV:

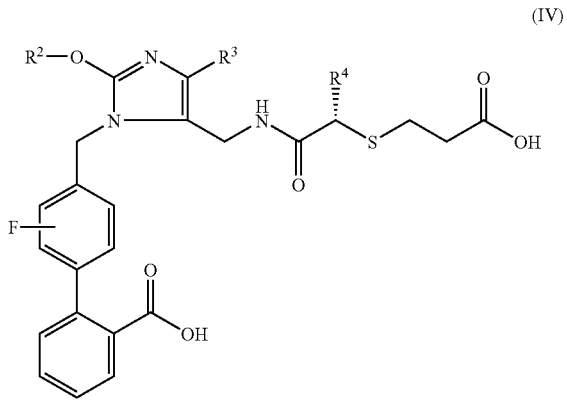

or a salt thereof.

In addition, particular compounds of formulas I, II, III and IV that are of interest include those set forth in the Examples as well as the salts thereof.

As used herein, the term "compound of the invention" includes all compounds encompassed by formulas I, II, III and IV. In addition, the compounds of the invention may also contain several basic or acidic groups (for example, amino or carboxyl groups) and therefore, such compounds can exist as a free base, free acid, or in various salt forms. All such salt forms are included within the scope of the invention. Accordingly, those skilled in the art will recognize that reference to a compound herein, for example, reference to a "compound of formula II" includes a compound of formula II as well as salts (for example, pharmaceutically acceptable salts) of that compound unless otherwise indicated. Furthermore, solvates are also included within the scope of this invention.

The compounds of the invention, as well as the compounds used in their synthesis, may also include isotopically-labeled compounds, that is, where one or more atoms have been enriched with atoms having an atomic mass different from the atomic mass predominately found in nature. Examples of isotopes that may be incorporated into the compounds of the invention, for example, include, but are not limited to, $^2H$, $^3H$, $^{13}C$, $^{14}C$, $^{15}N$, $^{18}O$, $^{17}O$, $^{35}S$, $^{36}Cl$, and $^{18}F$.

The nomenclature used herein to name the compounds of the invention is illustrated in the Examples, and has been derived using the commercially available AutoNom software (MDL, San Leandro, Calif.).

The bioanalytical methods of the invention are useful tools for determining the pK-pD relationship of compounds of formula I in a research laboratory setting. However, it is expected that these methods will also find utility in monitoring human patients that are undergoing treatment with a compound of formula I. Whether in a research laboratory setting, a hospital or a physician's office, a compound of formula I is first administered over a pre-set regimen, after which a biological test sample is obtained (for example, a blood sample is drawn) and tested for the presence of the compound or a derivatized form of the compound.

The compound of formula I can be administered by any acceptable route of administration including, but not limited to, oral, rectal, vaginal, nasal, inhaled, topical (including transdermal), ocular, and parenteral modes of administration.

The pre-set regimen can be, for example, a single dose (for example, in a laboratory setting), a single daily dose, multiple doses per day (for example, two, three, or four times daily), in a single weekly dose, etc.

In one embodiment, the method for detecting the presence of a compound of formula I in a biological test sample comprises the steps of: (a) collecting the sample from a mammal; (b) adding a derivatizing agent to the sample to form a derivatized compound; (c) subjecting the sample to chromatographic separation; and (d) detecting the presence of the derivatized compound, and correlating the presence of the derivatized compound to the presence of the compound of formula I. This method finds particular utility when detecting the amount of monomer that is present in a test sample. Compounds of formula I may form homodimers and/or may form heterodimers with sulfhydryl groups present in circulating proteins that are present in plasma. These dimers may not exhibit the full therapeutic benefit of the monomer compound of formula I, and therefore, one way to evaluate the therapeutic efficacy of a given dose is to detect only the amount of monomer present. Since the dimers do not contain a free sulfhydryl group, they do not react with the derivatizing agent and thus are not detected in step (d).

In another embodiment, the method for detecting the presence of a compound of formula I in a biological test sample comprises the steps of: (a) collecting the sample from a mammal; (b) adding a thiol reducing agent; (c) subjecting the sample to chromatographic separation; and (d) detecting the presence of a compound of formula I. This method finds particular utility when detecting the amount of administered compound of formula I that actually reaches the bloodstream. Thus, this method detects not only the amount of compound of formula I present in its monomer form, but also the amount present in a homodimer and/or heterodimer form. This method is also referred to as detecting the "total reducible monomer" of the compound of formula I that is present in a test sample. The addition of a reducing agent allows for the detection of the monomer as well as the reduced homodimers and heterodimers that may be present.

In one particular embodiment, the biological test sample is blood, and the method further comprises the steps of centrifuging the sample after step (b), and adding a second thiol reducing agent in the presence of an acid prior to step (c).

In some embodiments, it may be desirable to utilize both a reducing agent and a derivatizing agent. Typically, once the reducing agent is added, conditions of the sample environment are maintained so as to minimize or avoid re-dimerization, for example, by maintaining an acidic pH. However, the invention also contemplates adding a derivatizing agent at this stage to trap all monomer compounds, thereby preventing re-dimerization.

Collection

The collection step of the method relates to collecting a biological test sample from a mammal. Exemplary biological test samples include bile, blood, cells and cellular extracts, cerebral spinal fluid, mucus, plasma, saliva, semen, serum, sputum, stool, tears, tissue and tissue extracts, urine, and combinations thereof. In one embodiment, the test sample is blood. The term "mammals" is intended to include test subjects such as mice, rats, guinea pigs, rabbits, dogs, pigs, monkeys, and so forth, as well as human patients and human test subjects. In one embodiment, the mammal is selected from rats, dogs, monkeys, and humans.

The sample size will vary depending upon the mammal. For example, a 0.3 mL sample size is typical for blood samples taken from rats.

Derivatizing Agent

The method of the invention may comprise the step of adding a derivatizing agent to the sample. During this step, the sample is typically maintained at a pH that is compatible with the compound of formula I as well as the derivatizing agent, and will usually be in the pH range of plasma. In addition, the sample is typically maintained at room temperature.

The amount of derivatizing agent will vary depending upon the amount of the biological test sample. Generally, the volume ratio of the derivatizing agent to the test sample is about 1:100. Thus, about 3 µL of derivatizing agent would be used with a 0.3 mL test sample. In one embodiment, a significant excess of derivatizing agent is added to the sample to insure complete derivatization.

The biological test sample and derivatizing agent are mixed, and allowed to incubate at room temperature. The biological test sample is then evaluated in the next step, or may be placed on ice to await further processing, if desired.

A variety of derivatizing agents can be used in the method of the invention, including, by way of illustration and not limitation, acrylic acid esters, 1-benzyl-2-chloropyridinium bromide, 2-bromo-3'-methoxyacetophone, bromobimanes, p-bromophenacyl bromide, 4-(N,N-dimethylaminosulphonyl)-7-fluoro-2,1,3-benzoxadiazole (DBD-F), methyl-4-(6-methoxynapthalen-2-yl)-4-oxo-2-butenoate, maleimides, o-pthalaldehyde, and oxazole reagents. In one embodiment, the derivatizing agent is an acrylic acid ester.

Exemplary acrylic acid esters include methyl acrylate, ethyl acrylate, and butyl acrylates such as isobutyl acrylate. Corresponding derivatized compounds of formula II include those compounds where $R^5$ is —$CH_2CH_2C(O)O$—$C_{1-6}$alkyl or its hydrolyzed form, —$CH_2CH_2C(O)OH$. In one particular embodiment, the derivatizing agent is methyl acrylate.

Exemplary bimanes include bromobimanes such as p-sulfobenzolyloxy bromobimane, monobromobimane, and monobromotrimethyl ammoniobimane; chlorobimanes such as monochlorobimane; bimane iodoacetamide; and bimane $C_3$-maleimide. Bromobimanes are detailed in Kosower et al. (1978) *J. Amer. Chem. Soc.* 100:6518. The halomethyl group in bimanes such as monobromobimane and monochlorobimane, reacts with the sulfhydryl group to form a thioether and release the halide ion.

Exemplary maleimides include N-ethylmaleimide and analogs thereof, N-(4-benzoylphenyl]maleimide, N-[4-(6-dimethylamino-2-benzofuranyl)phenyl]maleimide, N-(7-dimethylamino-4-methyl-3-coumarinyl)maleimide, N-[p-(2-benzoxazolyl)phenyl]-maleimide (BOPM), and N-(1-pyrene)maleimide. Note, however, that the addition of a thiol compound to the carbon-carbon double bond of maleimides such as N-ethylmaleimide, will form a new chiral center on the N-ethylmaleimide side of the thiol adduct. Since compounds of formula I already contain a chiral center, two pairs of diastereomers will be generated as a result of reaction with N-ethylmaleimide. If the diastereomers are chromatographically resolved, there will be two peaks arising from the single thiol compound, which may lead to decreased assay sensitivity. Srinivas et al. (2003) *Biomedical Chromatography* 17:285-291.

Exemplary oxazole reagents include 2-chloro-4,5-bis(p-N,N-dimethylamino-sulphonylphenyl)oxazole.

Thiol Reducing Agent

The method of the invention may comprise the step of adding a thiol reducing agent to the sample. During this step, the sample is typically maintained at a pH that is compatible with the compound of formula I as well as the reducing agent, and will usually be in the pH range of plasma. In addition, the sample is typically maintained at room temperature.

The amount of reducing agent will vary depending upon the amount of the biological test sample. Generally, the final concentration of the reducing agent in the test sample is about 50 mM. Thus, about 5 µL of a 3M solution of reducing agent would be used with a 0.3 mL test sample.

A variety of thiol reducing agents can be used in the method of the invention, including, by way of illustration and not limitation, agents that contain sulfhydryl groups such as 1,4-dithiothreitol (DTT), 2-mercaptoethanol, and 2-mercaptoethylamine; phosphines and their derivatives, such as tris (2-carboxyethyl)phosphine (TCEP); and combinations thereof.

The biological test sample and reducing agent are mixed, and allowed to incubate at room temperature. The biological test sample is then evaluated in the next step, or may be placed on ice to await further processing, if desired. In one embodiment, the method involves adding a second reducing agent. This may also include acidifying the sample, for example with one of the acids described herein, such as formic acid. In one particular embodiment, the reducing agent is DTT. In another embodiment the first reducing agent is DTT, and the second reducing agent is TCEP.

Optional Sample Preparation

After the derivatizing agent and/or reducing agent is added to the biological test sample, the sample may undergo additional processing prior to chromatographic separation. Such sample preparation may serve to concentrate the compound being detected, it may remove endogenous materials or contaminants that may interfere with chromatography, and may serve to alter the biological matrix to an environment that is more compatible with the chromatographic separation technique being used. Exemplary sample preparation techniques include centrifugation, dilution, protein precipitation, dialysis, filtration, liquid-liquid extraction (LLE), solid phase extraction (SPE), and so forth.

In one embodiment, the test sample is blood and once the derivatizing agent and/or reducing agent is added, the blood is centrifuged to obtain plasma, the compounds of interest are extracted, and the extracts then reconstituted prior to undergoing chromatographic separation. For example, the compounds of interest can be extracted by protein precipitation, which involves diluting the sample with a protein precipitating agent. The sample is then vortexed and the resulting precipitated proteins are removed using filtration or centrifugation. The extracted material can then be reconstituted into a solvent that is compatible with the HPLC mobile phase. For those embodiments where a reducing agent is used, the extracted material can then be reconstituted by optionally including a second reducing agent.

Exemplary protein precipitating agents include acetic acid, acetone, acetonitrile, alginate, ammonium sulfate, carboxymethycellulose, chloroform, dextran, ethanol, formic acid, hydrochloric acid, methanol, polyacrylic acid, polyethylene glycol, polyphosphates, potassium chloride, sodium citrate, sulfuric acid, tannic acid, trichloroacetic acid, t-butanol, zinc chloride, and combinations thereof. One exemplary reconstituting solvent is 5% acetonitrile/water containing 0.2% formic acid.

Chromatographic Separation

Chromatographic separation can be done either before or after adding the derivatizing agent and/or reducing agent.

Thus, in one embodiment, the derivatizing agent and/or reducing agent is added to the test sample before the sample is subjected to chromatographic separation, for example, pre-column derivatization. In another embodiment, the derivatizing agent and/or reducing agent is added to the test sample after the sample is subjected to chromatographic separation, for example, post-column derivatization. Typically, however, chromatographic separation is done after the derivatizing agent and/or reducing agent is added.

Chromatographic separation can be accomplished by high performance liquid chromatography (HPLC), high performance liquid chromatography with mass spectrometry (LC/MS) or with tandem mass spectrometry (LC-MS/MS), MS/MS, electrospray ionization-mass spectrometry (ESI/MS) and so forth. In one particular embodiment, chromatographic separation is by LC-MS/MS, which is an analytical method that performs an additional mass spectrometry on a fragmented ion selected from the first mass spectrometry.

Detection

Detection of the compound of formula I or the derivatized compound of formula II can be qualitative (for example, if a labeling system is used) or quantitative. Typically, the method of the invention will comprise a quantitative detection step.

Multiple reaction monitoring (MRM) is the standard technique for quantitative LC-MS/MS experiments. In one embodiment of the monomer detection method, at least three specific MRM transitions are simultaneously monitored by LC-MS/MS: one for the internal standard, one for the compound of formula I, and one for the derivatized compound of formula II. Thus, the calibration curve can be established by plotting the peak area ratio of the derivatized compound of formula II/internal standard versus the concentration of each calibration standard. The relevant derivative concentrations of in vivo samples can then be determined from the calibration curve. This embodiment finds particular utility when the biological test sample is from a mammal such as a dog or monkey.

On the other hand, in some species such as rat for example, a compound of formula II where $R^5$ is —$CH_2CH_2C(O)O$—$C_{1-6}$alkyl (compound of formula III) hydrolyzes to form a compound of formula II where $R^5$ is —$CH_2CH_2C(O)OH$ (compound of formula IV). For such species, four specific MRM transitions are simultaneously monitored: one for the internal standard, one for the compound of formula I, one for the compound of formula III and one for the corresponding hydrolyzed compound of formula IV. For this embodiment, the calibration curve can be established by plotting the peak area ratio of the compound of formula IV/internal standard versus the concentration of each calibration standard.

For monomer detection methods, the concentration of the compound of formula II in the biological test sample can then be determined from the calibration curve. The concentration of the monomer compound of formula I (in ng/mL units) is then typically calculated from the concentration of the derivatized compound of formula II multiplied by the correction factor of the ratio of the molecular weight of the monomer compound of formula I to the molecular weight of the derivatized compound of formula II.

In one embodiment of the total reducible detection method, two specific MRM transitions are simultaneously monitored by LC-MS/MS: one for the internal standard and one for the compound of formula I. For this embodiment, the calibration curve can be established by plotting the peak area ratio of the compound of formula I/internal standard versus the concentration of each calibration standard. The concentration of the total reducible compound of formula I in the biological test sample can then be determined from the calibration curve.

Preparation of Calibration Standards and QC Samples

Calibration standards for methods detecting the amount of monomer, are typically prepared in a range of concentrations by spiking the specified amount of compound of formula II into a specified volume of blank biological test sample containing a derivatizing agent. Calibration standards for methods detecting the total reducible monomer are typically prepared in a range of concentrations by spiking the specified amount of compound of formula I into a specified volume of blank biological test sample containing a thiol reducing agent.

Compounds of formula I can be prepared by methods described in Examples 1-4. Compounds of formula II where $R^5$ is —$CH_2CH_2C(O)O$—$C_{1-6}$alkyl (compound of formula III) can be prepared by reacting a compound of formula I with an acrylic acid ester ($CH_2$=$CH_2$—$C(O)O$—$C_{1-6}$alkyl) such as methyl acrylate, ethyl acrylate, and butyl acrylate. One such preparation is described in Example 5.

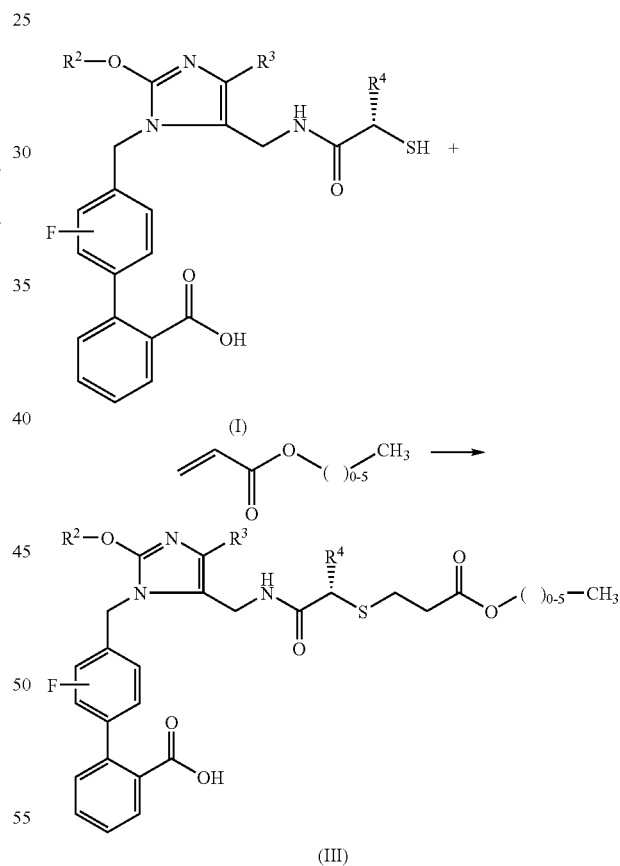

Compounds of formula II where $R^5$ is —$CH_2CH_2C(O)OH$ (compound of formula IV), can be prepared by hydrolysis of a compound of formula III.

In general, the calibration curve range is 0.1 to 1000 ng/mL of compound in the test sample. The highest concentration standard can be prepared by diluting 10 μL of 0.1 mg/mL stock solution to 990 μL of derivatizing agent-containing blank plasma or thiol reducing agent-containing blank plasma. The rest of the standards can be prepared from the highest concentration standard through serial dilutions with blank plasma containing derivatizing agent or thiol reducing agent. Several levels of QCs can be prepared in the derivatizing agent-containing blank plasma or thiol reducing agent-containing blank plasma in the same manner as calibration standards.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning.

DCC 1,3-dicyclohexylcarbodiimide
DCM dichloromethane or methylene chloride
DIPEA N,N-diisopropylethylamine
DMAP 4-dimethylaminopyridine
DMF N,N-dimethylformamide
DTT 1,4-dithiothreitol
EDC N-(3-dimethylaminopropyl)-N'-ethylcarbodiimide HCl
EDTA ethylenediaminetetraacetic acid
EtOAc ethyl acetate
EtOH ethanol
HOAt 1-hydroxy-7-azabenzotriazole
MA methyl acrylate
MeCN acetonitrile
MeOH methanol
NBS N-bromosuccinimide
QC quality control
TCEP tris(2-carboxyethyl)phosphine
TFA trifluoroacetic acid
THF tetrahydrofuran Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Reactions were worked up as described specifically in each preparation or example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument. HPLC analysis was conducted using an Agilent (Palo Alto, Calif.) Series 1100 instrument equipped with Zorbax Bonus RP 2.1×50 mm columns, supplied by Agilent, (a C14 column), having a 3.5 micron particle size. Detection was by UV absorbance at 214 nm. HPLC 10-70 data was obtained with a flow rate of 0.5 mL/minute of 10%-70% B over 6 minutes. Mobile phase A was 2%/98%/0.1% MeCN/H$_2$O/TFA; and mobile phase B was 90%/10%/0.1% MeCN/H$_2$O/TFA. Using the mobile phases A and B, HPLC 5-35 data and HPLC 10-90 data were obtained with a 5 minute gradient.

Preparation 1

(S)-2-Acetylsulfanyl-4-methylpentanoic Acid

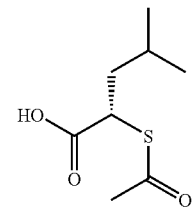

D-leucine (23.3 g, 177.3 mmol, 1.0 eq) was dissolved into 3.0M HBr in water (280 mL, 840 mmol) and cooled to 0° C. A solution of NaNO$_2$ (19.6 g, 284 mmol) in water (31.9 mL, 1.8 mol) was slowly added over 20 minutes and the mixture was stirred at 0° C. for 3 hours. The mixture was extracted with ethyl ether (2×500 mL), washed with water (100 mL) and saturated aqueous NaCl, dried over MgSO$_4$, filtered, and concentrated, to yield (R)-2-bromo-4-methylpentanoic acid as an off-yellow yellow oil (33.4 g).

Thioacetic acid (13.7 g, 180 mmol) and DMF (300 mL, 4 mol) were combined, and the mixture cooled in an ice bath. Sodium carbonate (19.0 g, 180 mmol) was added. After 30 minutes, (R)-2-bromo-4-methylpentanoic acid (33.4 g, 171 mmol) in DMF (20 mL) was added dropwise and the mixture was stirred at 0° C. to room temperature over 7 hours. The reaction was diluted with EtOAc (200 mL) and washed with a 1:1 saturated aqueous NaCl:1N HCl solution (200 mL). The layers were separated and the aqueous phase was extracted again with EtOAc (200 mL). The organics were combined, washed with saturated aqueous NaCl, dried over MgSO4, filtered, and concentrated under reduced pressure. The recovered oil was dissolved into diisopropyl ether (150 mL, 1.1 mol) and chilled at 0° C. Dicyclohexylamine (33.4 mL, 168 mmol) was added dropwise and the solid was allowed to precipitate out of solution. After stirring for an additional 30 minutes the material was filtered and washed with cold diisopropyl ether (150 mL). The recovered solid (41 g) was suspended in EtOAc (300 mL), 5% KHSO$_4$ (500 mL) was added, and the layers were separated. The organic was washed with saturated aqueous NaCl, dried over MgSO4, filtered, and concentrated under reduced pressure. The recovered oil was then azeotroped with toluene (3×50 mL) to yield the title compound as a yellow oil (20.7 g).

Preparation 2

5-Bromo-2-ethoxy-3H-imidazole-4-carbaldehyde

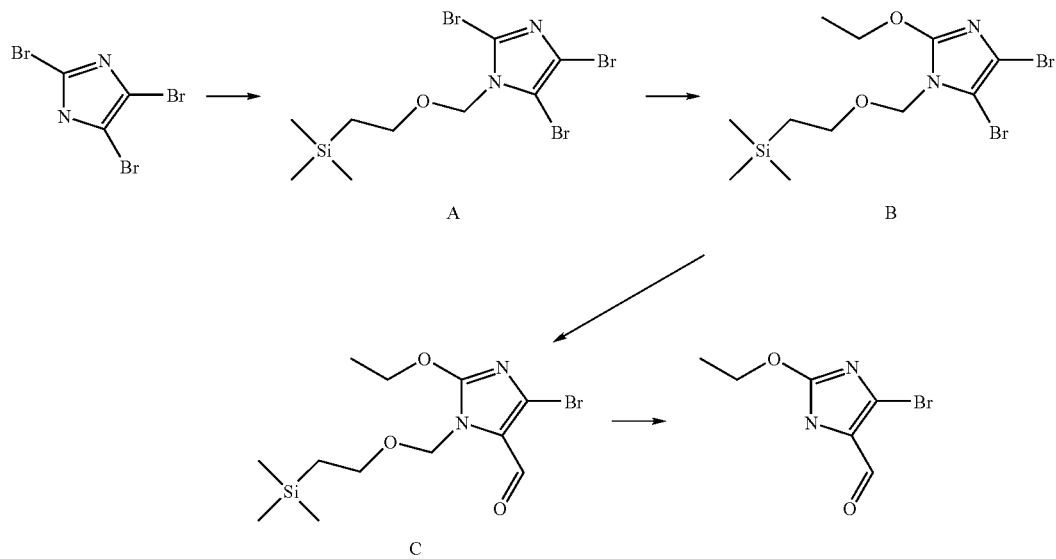

2,4,5-Tribromo-1H-imidazole (98.7 g, 324 mmol, 1.0 eq) was dissolved into DCM (1.2 L) and cooled to 0° C. To this was added DIPEA (62 mL, 360 mmol, 1.1 eq) followed by the slow addition of [β-(trimethylsilyl)ethoxy]methyl chloride (60.2 mL, 340 mmol, 1.05 eq). The solution was slowly warmed to room temperature. After 2 hours the mixture was washed with 1M $H_3PO_4$/saturated aqueous NaCl (1/10 mL; 2×600 mL). The organic layer was dried over $MgSO_4$, and evaporated to dryness, yielding compound A as faint yellow liquid that solidified on standing (137 g).

Compound A (130 g, 290 mmol, 1.0 eq) was dissolved in anhydrous ethanol (650 mL). To this was slowly added potassium t-butoxide (98.6 g, 879 mmol, 3.0 eq) and the mixture was heated to reflux for 16 hours. The mixture was then cooled to room temperature, filtered and concentrated. The resulting oil was dissolved in EtOAc (800 mL) and washed with saturated $NaHCO_3$ (400 mL). The layers were separated and the organic was washed with saturated aqueous NaCl, dried over $MgSO_4$, filtered and concentrated, yielding compound B as a brown oil (115.3 g). MS m/z: [M+H$^+$] calcd for $C_{11}H_{20}Br_2N_2O_2Si$, 401.9 found 401.2.

Compound B (69.5 g, 174 mmol, 1.0 eq) was dissolved in anhydrous THF (600 mL) and cooled to −78° C. under nitrogen. A 2.5M solution of n-butyllithium in hexanes (72.9 mL, 180 mmol, 1.05 eq) was added dropwise and the mixture was stirred at −78° C. for 10 minutes. DMF (40 mL, 520 mmol, 3.0 eq) was then added and the mixture was stirred at −78° C. for 15 minutes and was then warmed to room temperature. The reaction was quenched with water (10 mL), diluted with EtOAc (600 mL), and was washed with water (100 mL) and saturated aqueous NaCl, dried over $MgSO_4$ and concentrated under reduced pressure. The recovered material was purified by silica gel chromatography (15-30% EtOAc:hexanes) to produce compound C as a pale yellow oil (45 g).

Compound C (105.8 g, 303 mmol, 1.0 eq) was cooled at 0° C. in ice. TFA (300 mL) was added and the mixture was stirred at 0° C. for 15 minutes, then warmed to room temperature. After 90 minutes the mixture was concentrated under reduced pressure and redissolved in EtOAc (700 mL). The organic was washed with saturated bicarbonate (2×600 mL), saturated aqueous NaCl, dried over $MgSO_4$, and concentrated under reduced pressure to produce a yellow solid. The material was suspended in hexanes (300 mL) and stirred at 0° C. for 30 minutes. The material was filtered and the solid was washed with cold hexanes (150 mL) to yield the title compound as a pale white solid (61.2 g).

Preparation 3

4'-Bromomethyl-3'-fluorobiphenyl-2-carboxylic Acid t-Butyl Ester

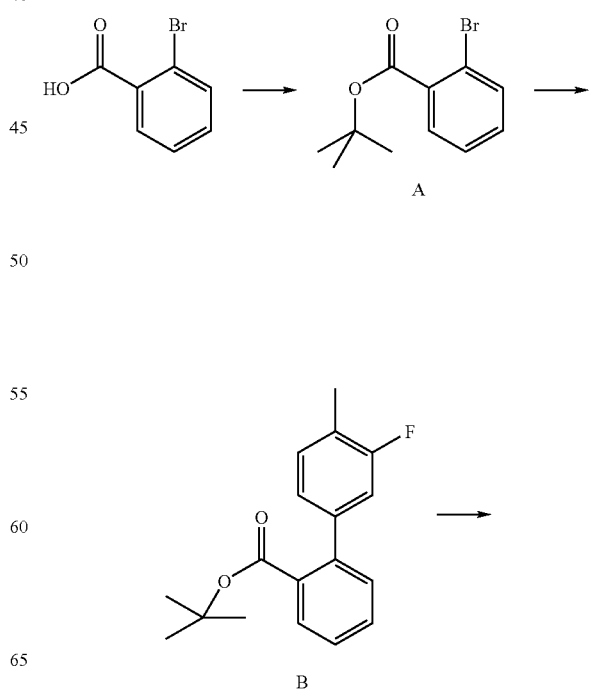

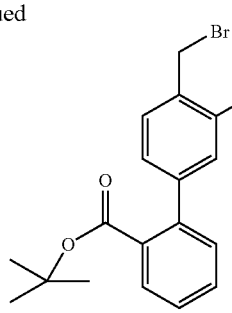

2-Bromobenzoic acid t-butyl ester (A): To a solution of DCC (32.8 g, 159 mmol) in DCM (200 mL, 2 mol) was added 2-bromobenzoic acid (32.0 g, 159 mmol) followed by DMAP (1.8 g, 15 mmol) and t-butyl alcohol (15.2 mL, 159 mmol). The mixture was stirred at room temperature for 16 hours, then filtered. The organic was washed with saturated NaHCO₃ (200 mL), saturated aqueous NaCl, dried over MgSO₄, filtered and concentrated under reduced pressure to yield compound A as an oil (41.6 g).

3'-Fluoro-4'-methylbiphenyl-2-carboxylic acid t-butyl ester (B): Compound A (80.0 g, 311 mmol) and 3-fluoro-4-methylphenylboronic acid (52.7 g, 342 mmol) were suspended in isopropyl alcohol (260 mL, 3.5 mol). A solution of sodium carbonate (56.1 g, 529 mmol) in water (260 mL, 15 mol) was added and the mixture was degassed under nitrogen. Tetrakis(triphenylphosphine)palladium(0) (3.6 g, 3.1 mmol) was then added and the mixture was stirred at 90° C. for 17 hours. The mixture was concentrated under reduced pressure and suspended in water (200 mL). The aqueous phase was extracted with EtOAc (600 mL) and separated. The organic phase was washed with saturated aqueous NaCl and concentrated under reduced pressure. The recovered oil was purified by silica gel chromatography (4-6% 5×120 g column) to yield compound B as a clear oil (68.2 g).

Compound B (92.9 g, 324 mmol) was dissolved in CCl₄ (730 mL, 7.6 mol) and degassed under nitrogen. NBS (57.7 g, 324 mmol) was added, followed by benzoyl peroxide (2.0 g, 8.1 mmol) and the mixture was heated at 90° C. under nitrogen for 30 minutes, then cooled in an ice bath. A saturated aqueous Na₂SO₃ solution (500 mL) was added and the mixture was stirred overnight and allowed to warm to room temperature. The mixture was filtered and the layers were separated. The organic layer was washed with saturated aqueous Na₂SO₃ then with water, was dried with MgSO4, filtered, and concentrated. The crude oil was triturated with 3% EtOAc:hexanes (150 mL) and cooled in an ice bath. The solids were filtered, rinsed with cold 3% EtOAc:hexanes (2×200 mL), and dried to yield the title compound as a white solid (39.2 g, 91.6% purity).

Preparation 4
4'-(4-Bromo-2-ethoxy-5-formylimidazol-1-ylmethyl)-3'-fluorobiphenyl-2-carboxylic Acid t-Butyl Ester

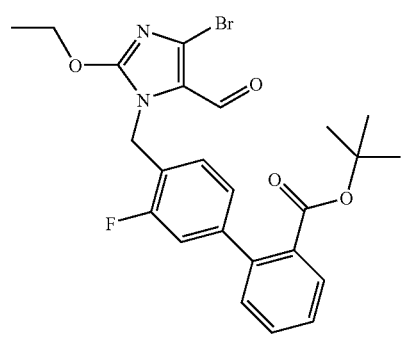

5-Bromo-2-ethoxy-3H-imidazole-4-carbaldehyde (10.0 g, 45.6 mmol), 4'-bromomethyl-3'-fluorobiphenyl-2-carboxylic acid t-butyl ester (16.7 g, 45.6 mmol) and potassium carbonate (9.5 g, 68.5 mmol) were dissolved in DMF (200 mL) at 0° C. After 10 minutes, the mixture was allowed to warm to room temperature and was stirred overnight. The mixture was filtered and concentrated in vacuo. The concentrate was extracted with EtOAc (2×200 mL) and sat. aq. NaHCO₃: water; 1:1 (150 mL). The combined organic fractions were dried over Na₂SO₄, filtered, and concentrated in vacuo. The crude material was recrystallized from EtOH (20 mL) and water (40 mL) to afford a white solid. The filtrate was concentrated in vacuo and purified by silica gel chromatography (EtOAc:hexanes) to yield the title compound as a white solid (3.6 g).

Preparation 5
4'-(5-Aminomethyl-2-ethoxy-4-ethylimidazol-1-ylmethyl)-3'-fluorobiphenyl-2-carboxylic Acid t-Butyl Ester

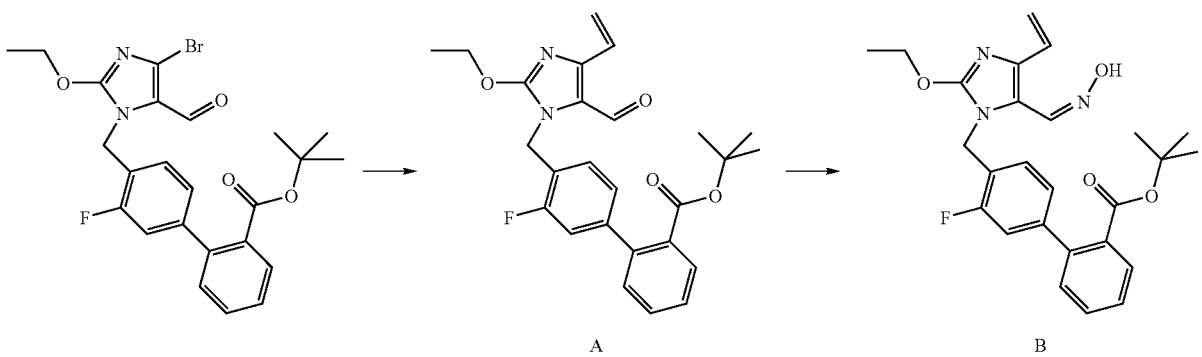

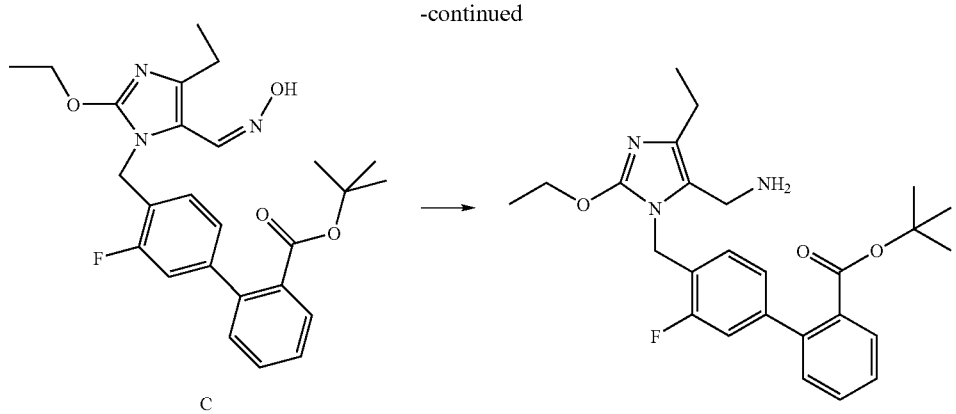

C

4'-(2-Ethoxy-5-formyl-4-vinyl-imidazol-1-ylmethyl)-3'-fluorobiphenyl-2-carboxylic acid t-butyl ester (A): 4'-(4-Bromo-2-ethoxy-5-formylimidazol-1-ylmethyl)-3'-fluorobiphenyl-2-carboxylic acid t-butyl ester (30.0 g, 59.6 mmol), 2,4,6-trivinylcyclo-triboroxane pyridine complex (5.74 g, 23.8 mmol), tetrakis(triphenylphosphine) palladium(0) (689 mg, 596 μmol), potassium carbonate (8.2 g, 59.6 mmol), 1,2-dimethoxyethane (266 mL, 2560 mmol), and water (107 mL, 5960 mmol) were combined. The solution was heated at 90° C. for 4 hours. After cooling to room temperature, EtOAc (300 mL) and water (100 mL) was added. The organic layer was dried over $Na_2SO_4$, filtered, and concentrated in vacuo. The product was purified by silica gel chromatography (5-30% EtOAc:hexanes) to yield compound A (22.5 g).

4'-[2-Ethoxy-5-(hydroxyiminomethyl)-4-vinylimidazol-1-ylmethyl]-3'-fluoro-biphenyl-2-carboxylic acid t-butyl ester (B): A solution of compound A (17.9 g, 39.7 mmol), hydroxylamine (3.9 g, 119 mmol), pyridine (200 mL), and water (100 mL) were combined. After stirring overnight, water (50 mL) was added and the precipitate was filtered to yield compound B as an off-white solid (16.9 g).

4'-[2-Ethoxy-4-ethyl-5-(hydroxyiminomethyl)imidazol-1-ylmethyl]-3'-fluoro-biphenyl-2-carboxylic acid t-butyl ester (C): Compound B (1.0 g, 2.2 mmol) was dissolved in EtOH (54 mL, 940 mmol), and added to a flask containing palladium (200 mg, 2 mmol) in 10 mL of EtOH. The mixture was degassed and stirred under hydrogen for 1 hour. The palladium was filtered and the solvent was concentrated to yield compound C (1.0 g), which was immediately carried on to the next reaction.

Compound C (1.0 g, 2.1 mmol), sodium cyanoborohydride (538 mg, 8.6 mmol), and ammonium acetate (659 mg, 8.6 mmol) were dissolved in MeOH. The mixture was cooled at 0° C. and stirred for 15 minutes before titanium(III) chloride (1.3 g, 8.6 mmol) was added. The mixture was stirred at 0° C. for 10 minutes, then warmed to room temperature and stirred for 4 hours. Ammonium hydroxide was added (75 mL) and the mixture was stirred at room temperature overnight. Saturated sodium bicarbonate (75 mL) was then added and the product extracted with DCM (4×), dried over $MgSO_4$, filtered, and concentrated. The product was then purified by flash chromatography (0-10% MeOH:DCM) to yield the title compound (600 mg).

Example 1

4'-{2-Ethoxy-4-ethyl-5-[((S)-2-mercapto-4-methylpentanoylamino)methyl]-imidazol-1-ylmethyl}-3'-fluorobiphenyl-2-carboxylic Acid

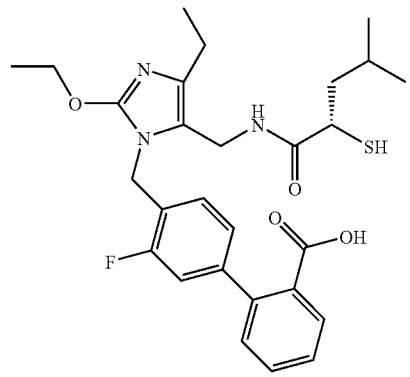

4'-{5-[((S)-2-Acetylsulfanyl-4-methylpentanoylamino)methyl]-2-ethoxy-4-ethylimidazol-1-ylmethyl}-3'-fluorobiphenyl-2-carboxylic acid t-butyl ester: 4'45-Aminomethyl-2-ethoxy-4-ethylimidazol-1-ylmethyl)-3'-fluorobiphenyl-2-carboxylic acid t-butyl ester (2.0 g, 4.4 mmol), (S)-2-acetylsulfanyl-4-methylpentanoic acid (839 mg, 4.4 mmol), 4-methylmorpholine (484.8 μL, 4.4 mmol), and HOAt (600 mg, 4.4 mmol) were combined and dissolved in DMF (50 mL, 640 mmol), and cooled at 0° C. for 10 minutes. EDC (780 μL, 4.4 mmol) was then added and the mixture was stirred at 0° C. for 1 hour and then at room temperature for 1 hour. The reaction was quenched with water (100 mL), and the mixture was extracted with EtOAc (400 mL) and concentrated. The product was purified by column chromatography (0-50% EtOAc in hexanes) to obtain the acetylsulfanyl ester intermediate (2.7 g).

4'-{5-[((S)-2-Acetylsulfanyl-4-methylpentanoylamino)methyl]-2-ethoxy-4-ethylimidazol-1-ylmethyl}-3'-fluorobiphenyl-2-carboxylic acid: The acetylsulfanyl ester intermediate was dissolved in DCM:TFA (20 mL each), stirred at room temperature for 3 hours, and then concentrated. The residue was taken up in EtOAc and was washed with a saturated sodium bicarbonate solution and then dried over MgSO₄, and concentrated to yield the acetylsulfanyl acid intermediate (2.0 g).

The acetylsulfanyl acid intermediate was dissolved in MeOH and the solution was degassed, stirred under nitrogen, and cooled at 0° C. 0.5M Sodium methoxide in MeOH (13.3 mL, 6.7 mmol, 2 equivalents based on the amount of acid intermediate present) was added and the mixture was stirred at 0° C. under nitrogen for 20 minutes. The mixture was then acidified with 1N HCl (10.0 mL to a pH~4). The product was concentrated, dissolved in EtOAc, washed with water, dried over MgSO₄, filtered, and then concentrated. The product was purified by preparative HPLC (20-40% MeCN:water w/0.5% TFA 70 minute method) to yield the title compound as a TFA salt (1.1 g, 97.7% purity). MS m/z: [M+H$^+$] calcd for C$_{28}$H$_{34}$FN$_3$O$_4$S, 528.23; found 528.2.

Preparation 6

4'-(5-Aminomethyl-4-cyclopropyl-2-ethoxy-imidazol-1-ylmethyl)-3'-fluorobiphenyl-2-carboxylic Acid t-Butyl Ester

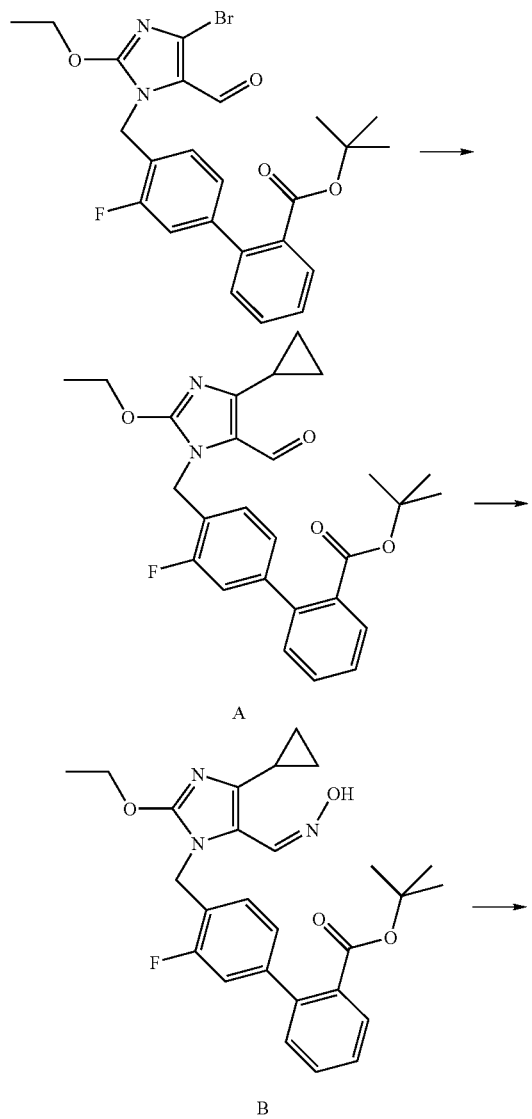

A

B

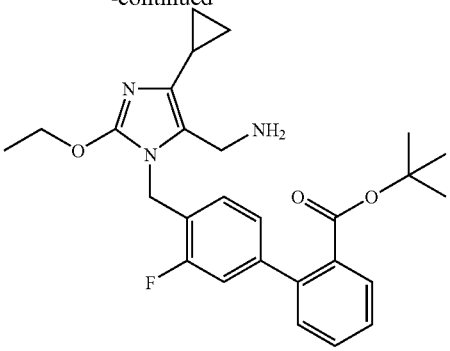

4'-(4-Cyclopropyl-2-ethoxy-5-formylimidazol-1-ylmethyl)-3'-fluoro-biphenyl-2-carboxylic acid t-butyl ester (A): 4'-(4-Bromo-2-ethoxy-5-formylimidazol-1-ylmethyl)-3'-fluorobiphenyl-2-carboxylic acid t-butyl ester (2.6 g, 5.24 mmol), cyclopropylboronic acid (900 mg, 10.5 mmol) 1.0 M tricyclohexylphosphine in toluene (524 μL, 524 μmol), potassium phosphate (3.9 g, 18.4 mmol), and palladium acetate (118 mg, 524 μmol) were combined and dissolved in toluene (95.0 mL, 892 mmol). The mixture was stirred at room temperature under nitrogen for 20 minutes. Water (5.1 mL, 183 mmol) and potassium carbonate (2.5 g, 18.4 mmol) were then added and the mixture heated at 100° C. for 3 hours. Water (100 mL) was added and the layers separated. The organics were washed with water (50 mL) and saturated aqueous NaCl (50 mL), dried over Na₂SO₄, and the solvent evaporated. The product was purified by flash chromatography (0-40% EtOAc in hexanes to yield compound A (1.2 g).

4'-[4-Cyclopropyl-2-ethoxy-5-(hydroxyiminomethyl)imidazol-1-ylmethyl]-3'-fluorobiphenyl-2-carboxylic acid t-butyl ester (B): Compound A (1.21 g, 2.60 mmol), hydroxylamine hydrochloride (181 mg, 2.6 mmol), pyridine (10 mL, 100 mmol), and MeOH (10 mL, 300 mmol) were combined and stirred at room temperature overnight. Additional hydroxylamine hydrochloride (20 mg) was added and the mixture evaporated to dryness. The solids were dissolved in DCM (50 mL), washed with water (2×20 mL) and saturated aqueous NaCl (10 mL), dried over Na₂SO₄, and evaporated to dryness to afford compound B as a white solid (1.0 g).

Compound B (4.5 g, 9.4 mmol), sodium cyanoborohydride (3 g, 46.9 mmol) and ammonium acetate (3.6 g, 46.9 mmol) were dissolved in MeOH. The mixture was cooled at 0° C. and stirred for 15 minutes before titanium(III) chloride (7.2 g, 46.9 mmol) was added. The mixture was stirred at 0° C. for 10 minutes, then warmed to room temperature and stirred for 4 hours. Ammonium hydroxide (200 mL) was added and the mixture was stirred at room temperature overnight. The product was then extracted with DCM (5×100 mL), dried over MgSO₄, filtered and concentrated. The product was then purified by column chromatography (0-10% MeOH in DCM) to yield the title compound (3.5 g).

Example 2

4'-{4-Cyclopropyl-2-ethoxy-5-[((S)-2-mercapto-4-methylpentanoylamino)-methyl]imidazol-1-ylmethyl}-3'-fluorobiphenyl-2-carboxylic Acid

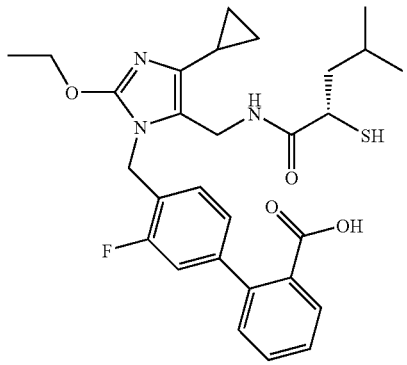

4'-{5-[((S)-2-Acetylsulfanyl-4-methylpentanoylamino) methyl]-4-cyclopropyl-2-ethoxyimidazol-1-ylmethyl}-3'-fluoro-biphenyl-2-carboxylic acid t-butyl ester: 4'-(5-Aminomethyl-4-cyclopropyl-2-ethoxy-imidazol-1-ylmethyl)-3'-fluorobiphenyl-2-carboxylic acid t-butyl ester (11.9 g, 25.6 mmol), (S)-2-acetylsulfanyl-4-methylpentanoic acid (4.9 g, 25.6 mmol), 4-methylmorpholine (2.8 mL, 25.6 mmol), and HOAt (3.5 g, 25.6 mmol) were combined and dissolved in DMF (120 mL, 1.5 mol) and was cooled at 0° C. for 10 minutes. Then EDC (4.5 mL, 25.6 mmol) was added and the mixture was stirred at 0° C. for 1 hour, then at room temperature for 2 hours. The reaction was quenched with water (100 mL), and the product extracted with EtOAc (100 mL) and concentrated. The residue was purified by column chromatography (0-50% EtOAc in hexanes) to obtain the acetylsulfanyl ester intermediate (10.7 g).

4'-{5-[((S)-2-Acetylsulfanyl-4-methylpentanoylamino) methyl]-4-cyclopropyl-2-ethoxyimidazol-1-ylmethyl}-3'-fluorobiphenyl-2-carboxylic acid: The acetylsulfanyl ester intermediate was dissolved in DCM:TFA (10 mL each) and was stirred at room temperature for 3 hours, then concentrated. The residue was taken up in EtOAc, washed with a saturated sodium bicarbonate solution, dried over MgSO$_4$, and concentrated to yield the acetylsulfanyl acid intermediate.

The acetylsulfanyl acid intermediate was dissolved in MeOH (30 mL) and the solution was degassed, stirred under nitrogen and cooled at 0° C. 0.5M Sodium methoxide in MeOH (60 mL, 2 equivalents based on the amount of acid intermediate that was present) was added and the mixture was stirred at 0° C. under nitrogen for 20 minutes. The mixture was then acidified with 1N HCl (15 mL). The product was concentrated, dissolved in EtOAc, washed with water, dried over MgSO$_4$, filtered and then concentrated. The product was purified by preparative HPLC (20-40% a MeCN:water w/0.5% TFA 70 minute method) to yield the title compound as a TFA salt (5.8 g, 98% purity). MS m/z: [M+H$^+$] calcd for C$_{29}$H$_{34}$FN$_3$O$_4$S, 540.23; found 540.4.

Preparation 7

5-Bromo-2-propoxy-3H-imidazole-4-carbaldehyde

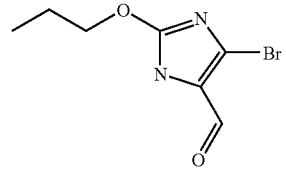

5-Bromo-2-propoxy-3-(2-trimethylsilanylethoxymethyl)-3H-imidazole-4-carbaldehyde (43.6 g, 120 mmol) was cooled at 0° C. in ice. TFA (200 mL, 2 mol) was added and the mixture was stirred at 0° C. for 15 minutes, then warmed to room temperature. After 20 minutes, the mixture was concentrated under reduced pressure and redissolved in EtOAc (300 mL). The organic was washed with saturated bicarbonate (200 mL), saturated aqueous NaCl, dried over MgSO$_4$ and concentrated under reduced pressure to produce the title compound (28.6 g) as a yellow solid, which was used without further purification.

Preparation 8

4'-(5-Aminomethyl-2-propoxy-4-ethylimidazol-1-ylmethyl)-3'-fluorobiphenyl-2-carboxylic acid t-Butyl Ester

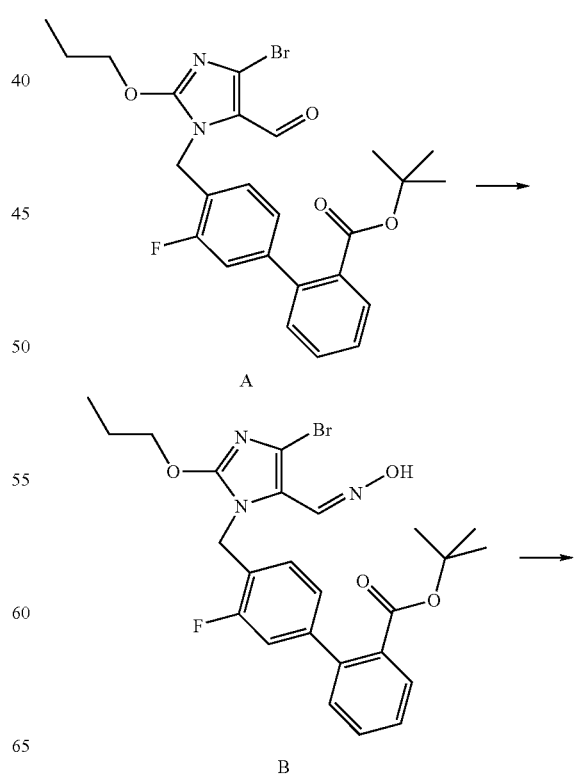

-continued

Compound C (3.2 g) was dissolved in EtOAc (150 mL) and MeOH (50 mL), followed by the addition of concentrated sulfuric acid (500 μL). 10% Pd/C, Degussa type, (200% by mass) was then added and the mixture was degassed with nitrogen (2×) and then stirred at room temperature under hydrogen for 1-2 hours. The mixture was then degassed with nitrogen and the palladium was filtered off. The material was basified with 10N NaOH, the solvent was evacuated, the solids washed with EtOAc and saturated aqueous NaCl, followed by drying over MgSO$_4$. The material was then filtered and evacuate to dryness to obtain the title compound (1.9 g), which was used without further purification.

Example 3

4'-{4-Ethyl-5-[((S)-2-mercapto-4-methylpentanoylamino)methyl]-2-propoxyimidazol-1-ylmethyl}-3'-fluorobiphenyl-2-carboxylic Acid

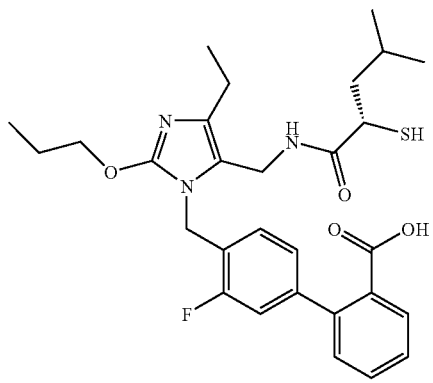

4'-(4-Bromo-5-formyl-2-propoxyimidazol-1-ylmethyl)-3'-fluorobiphenyl-2-carboxylic acid t-butyl ester (A): 5-Bromo-2-propoxy-3H-imidazole-4-carbaldehyde (2.1 g, 8.8 mmol), 4'-bromomethyl-3'-fluorobiphenyl-2-carboxylic acid t-butyl ester (3.2 g, 8.8 mmol) and potassium carbonate (3.6 g, 26.4 mmol) were dissolved in DMF (100 mL). The solution was stirred until the reaction was complete, as determined by HPLC. The mixture was extracted with EtOAc (200 mL), washed with saturated aqueous NaCl (4×100 mL), dried over MgSO$_4$, evacuated to dryness, and purified by flash chromatography (EtOAc/hexanes) to yield compound A (4.5 g).

4'-[4-Bromo-5-(hydroxyiminomethyl)-2-propoxy-imidazol-1-ylmethyl]-3'-fluorobiphenyl-2-carboxylic acid t-butyl ester (B): Compound A (4.5 g) was dissolved in pyridine (80 mL). Hydroxylamine hydrochloride (1.8 g, 26.4 mmol) was added, followed by sufficient water to dissolve the solids. The mixture was stirred at room temperature overnight. The solids were filtered, washed with water, and dried under vacuum to yield compound B (4.0 g).

3'-Fluoro-4'-[5-(hydroxyiminomethyl)-2-propoxy-4-vinyl-imidazol-1-ylmethyl]-biphenyl-2-carboxylic acid t-butyl ester (C): Compound B (4.0 g), tetrakis(triphenyl-phosphine) palladium(0) (203 mg, 176 μmol) and 1,2-dimethoxyethane (100 Ml, 1 mol) were combined and stirred under nitrogen at room temperature for 20 minutes. Water (20.6 mL, 1.1 mol), 2,4,6-trivinylcyclotriboroxane pyridine complex (1.1 g, 44.4 mmol) and potassium carbonate (1.3 g, 9.3 mmol) were then added and the mixture was heated at 90° C. for 6-12 hours. The product was purified by flash chromatography in hexanes/EtOAc 0-75%) to yield compound C (3.2 g).

4'-{5-[((S)-2-Acetylsulfanyl-4-methylpentanoylamino) methyl]-4-ethyl-2-propoxyimidazol-1-ylmethyl}-3'-fluorobiphenyl-2-carboxylic acid t-butyl ester: 4'-(5-Aminomethyl-2-propoxy-4-ethylimidazol-1-ylmethyl)-3'-fluorobiphenyl-2-carboxylic acid t-butyl ester (8.0 g, 17 mmol), (S)-2-acetylsulfanyl-4-methylpentanoic acid (3.3 g, 17.1 mmol), 4-methylmorpholine (1.98 mL, 17.1 mmol), and HOAt (2.3 g, 17.1 mmol) were combined and dissolved in DMF (198.7 mL, 2566 mmol). The mixture was cooled at 0° C. for 10 minutes, then EDC (3.0 mL, 17.1 mmol) was added. The mixture was stirred at 0° C. for 1 hour and then at room temperature for 1 hour, then EtOAc (200 mL) was added. The organic layer was washed with 1 N HCl (100 mL), NaHCO$_3$ (100 mL), then saturated aqueous NaCl (100 mL). The organic layer was dried over MgSO$_4$, filtered and evacuated to dryness to obtain the acetylsulfanyl ester intermediate (7 g).

Acid deprotection was accomplished by dissolving the acetylsulfanyl ester intermediate in DCM and adding an equal amount of TFA while in an ice bath. The mixture was dried under vacuum, the reside taken up in toluene and vacuum dried again. The material was dissolved in THF, under nitrogen, and NaOCH$_3$ added to make the solution basic. The reaction was monitored closely over 1 hour until final deprotection was complete. The product was purified using reverse phase chromatography on a gradient of 20-55% to give the title compound as a TFA salt (3.5 g). MS m/z: [M+H⁺] calcd for $C_{29}H_{36}FN_3O_4S$, 542.25; found 542.6.

Preparation 9

4'-Bromomethyl-2'-fluorobiphenyl-2-carboxylic Acid t-Butyl Ester

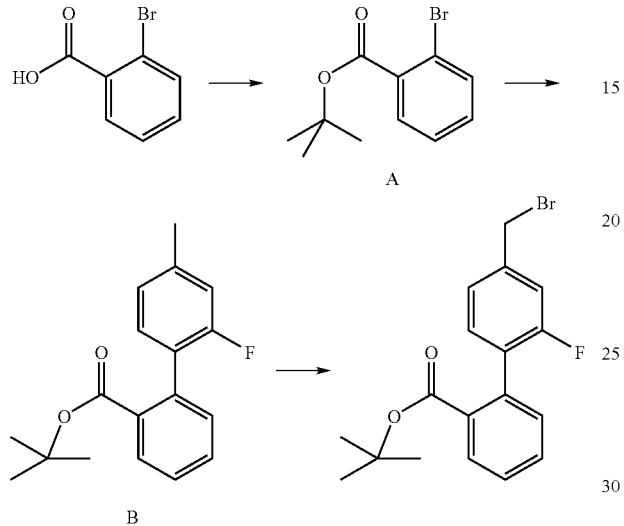

2-Bromobenzoic acid t-butyl ester (A): 2-Bromobenzoic acid (203.2 g, 1011 mmol) was added to a solution of 1.0 M DCC in DCM (1011 mL, 1011 mmol) and cooled at 0° C. DMAP (11.36 g, 93.0 mmol) and t-butyl alcohol (106.3 mL, 1112 mmol) were added and the mixture was stirred at room temperature for 10 minutes, then warmed to room temperature and stirred overnight. The mixture was then filtered, washed with saturated $NaHCO_3$ (200 mL), saturated aqueous NaCl, dried over $MgSO_4$, filtered and concentrated under reduced pressure to yield compound A as a clear oil (168.4 g).

2'-Fluoro-4'-methylbiphenyl-2-carboxylic acid t-butyl ester (B): Compound A (22.8 g, 88.6 mmol) and 2-fluoro-4-methylphenylboronic acid (15.0 g, 97.4 mmol) were suspended in isopropyl alcohol (75 mL, 980 mmol). A solution of sodium carbonate (16 g, 150 mmol) in water (75 mL, 4.2 mol) was added and the mixture was degassed under nitrogen. Tetrakis(triphenylphosphine)palladium(0) (1.0 g, 880 μmol) was then added and the mixture was stirred at 90° C. overnight. The mixture was cooled to room temperature, EtOAc (200 mL) and water (200 mL) were added, and the mixture was filtered. The liquor was extracted with EtOAc (2×100 mL), washed with saturated aqueous NaCl, dried over $MgSO_4$, filtered and concentrated. The material was purified by flash chromatography (0-15% EtOAc in hexanes) to yield compound B as a colorless oil (14.9 g, 96% purity).

Compound B (14.9 g, 52.0 mmol) was dissolved in $CCl_4$ (100 mL, 1.1 mol) and degassed under nitrogen. NBS (8.8 g, 49 mmol) was added, followed by benzoyl peroxide (250 mg, 1.0 mmol) and the mixture was heated at 90° C. under nitrogen. After 6 hours, the mixture was cooled to room temperature, filtered and concentrated to yield a yellow oil (19.4 g). The oil was taken up in 3% EtOAc in hexanes (25 mL) and stored at −20° C. overnight. The material was then warmed to room temperature, filtered and concentrated to yield the title compound as a yellow oil (18.1 g, 83% purity).

Preparation 10

4'-(5-Aminomethyl-4-ethyl-2-propoxyimidazol-1-ylmethyl)-2'-fluorobiphenyl-2-carboxylic Acid t-Butyl Ester

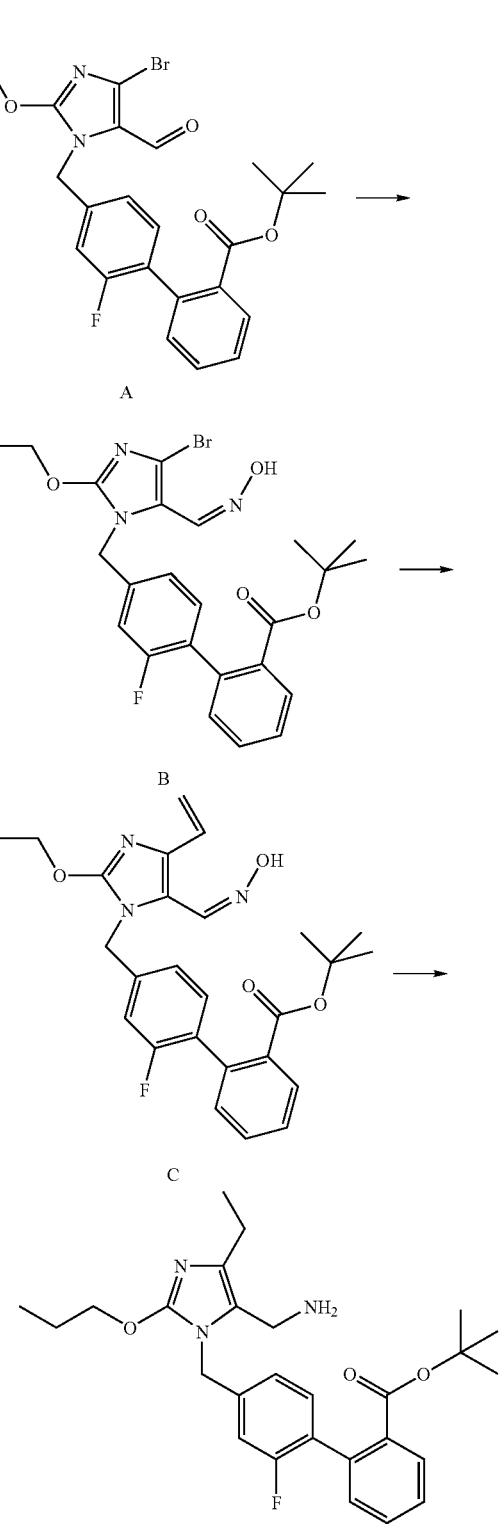

4'-(4-Bromo-5-formyl-2-propoxyimidazol-1-ylmethyl)-2'-fluorobiphenyl-2-carboxylic acid t-butyl ester (A): 5-Bromo-2-propoxy-3H-imidazole-4-carbaldehyde (3.7 g, 15.7 mmol), 4'-bromomethyl-2'-fluorobiphenyl-2-carboxylic acid t-butyl ester (5.7 g, 15.7 mmol) and potassium carbonate (6.5 g, 47.0 mmol) were dissolved in DMF (50 mL, 646 mmol), and stirred at room temperature until the reaction was complete, as determined by HPLC. Water (100 mL) was added and the mixture was extracted with EtOAc (2×), washed with saturated aqueous NaCl (2×), dried over $MgSO_4$, filtered and concentrated to yield a yellow oil. The oil was purified by flash chromatography (2-20% EtOAc/hexanes) to yield compound A (4.8 g) as a colorless oil.

4'-[4-Bromo-5-(hydroxyiminomethyl)-2-propoxyimidazol-1-ylmethyl]-2'-fluoro-biphenyl-2-carboxylic acid t-butyl ester (B): Compound A (4.7 g, 9.0 mmol), hydroxylamine hydrochloride (943 mg, 13.6 mmol), pyridine (60 mL, 740 mmol), and water (30 mL, 1.7 mol) were combined and stirred at room temperature overnight. Additional water (30 mL) was added, and the solids were filtered, washed with water, and dried to yield compound B (4.4 g) as a white solid, which was used without further purification.

2'-Fluoro-4'-[5-(hydroxyiminomethyl)-2-propoxy-4-vinylimidazol-1-ylmethyl]-biphenyl-2-carboxylic acid t-butyl ester (C): Compound B (4.3 g, 8.2 mmol), tetrakis(triphenylphosphine)palladium(0) (565 mg, 489 μmol), 1,2-dimethoxyethane (82 mL, 790 mmol), water (8.2 mL, 450 mmol), 2,4,6-trivinylcyclotriboroxane pyridine complex (1.2 g, 6.5 mmol), and potassium carbonate (1.2 g, 8.6 mmol) were combined and the mixture heated at 90° C. under nitrogen for 4 hours. The mixture was cooled to room temperature. Water (100 mL) and EtOAc (100 mL) were added and the insoluble material was filtered away. Saturated aqueous NaCl (50 mL) was added. The aqueous layer was extracted with EtOAc (2×), washed with saturated aqueous NaCl (2×), dried over $MgSO_4$, filtered, and concentrated to yield a yellow semisolid material (4.5 g) The product was purified by flash chromatography (2-30% EtOAc/hexanes) to yield compound C (2.2 g) as a white solid.

A solution of Compound C (1.6 g, 3.2 mmol) in EtOAc (48 mL, 490 mmol), MeOH (16 mL, 410 mmol), and sulfuric acid (190 μL, 3.6 mmol) was added to 10% Pd/C, Degussa type, wet 50% (0.05:0.45:0.5, palladium:carbon black:water, 3.10 g, 1.46 mmol) under nitrogen. The mixture was stirred at room temperature under hydrogen for 1 hour. Additional 10% Pd/C, Degussa type, wet 50% (1.6 g) was added. After 2 hours, the palladium was filtered off, and the material was rinsed with EtOAc and MeOH then combined with another lot of the title compound. The mixture was then basified with saturated bicarbonate and concentrated. The material was then taken up with EtOAc, washed with saturated aqueous NaCl, dried over $MgSO_4$, filtered and concentrated to yield the title compound (1.5 g) as a yellow oil, which was used without further purification.

Example 4

4'-{4-Ethyl-5-[((S)-2-mercapto-4-methylpentanoylamino)methyl]-2-propoxyimidazol-1-ylmethyl}-2'-fluorobiphenyl-2-carboxylic Acid

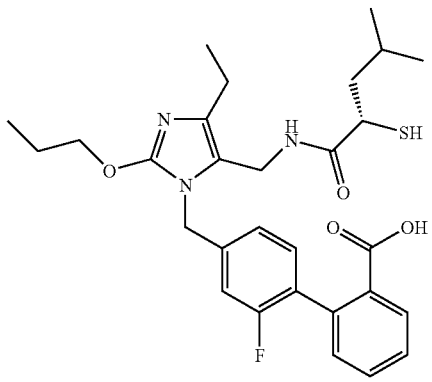

4'-{5-[((S)-2-Acetylsulfanyl-4-methylpentanoylamino)methyl]-4-ethyl-2-propoxyimidazol-1-ylmethyl}-2'-fluoro-biphenyl-2-carboxylic acid t-butyl ester: 4'45-Aminomethyl-4-ethyl-2-propoxyimidazol-1-ylmethyl)-2'-fluorobiphenyl-2-carboxylic acid t-butyl ester (1.5 g, 3.2 mmol), HOAt (434 mg, 3.2 mmol), and 4-methylmorpholine (350 μL, 3.2 mmol) were dissolved in DMF (22.6 mL, 292 mmol) and cooled at 0° C. for 10 minutes. EDC (564 μL, 3.2 mmol) was added, followed by the addition of a solution of (S)-2-acetylsulfanyl-4-methylpentanoic acid (606 mg, 3.2 mmol) in DMF (1.5 mL). After 30 minutes the mixture was warmed to room temperature. Water (30 mL) was added. after 150 minutes, and the mixture was extracted with EtOAc (2×), washed with saturated aqueous NaCl, dried over $MgSO_4$, filtered and concentrated to yield a crude yellow oil (2.2 g), which was purified by flash chromatography (0-50% EtOAc/hexanes) to obtain the acetylsulfanyl ester intermediate as a white semisolid (1.2 g).

Acid deprotection was accomplished by dissolving the acetylsulfanyl ester intermediate in DCM (20 mL, 320 mmol). TFA (20 mL, 260 mmol) was added. After 50 minutes, the reaction was complete (as determined by HPLC) and the material was concentrated. The crude material was taken up in MeOH (10 mL) and cooled at 0° C. under nitrogen, followed by the addition of 0.5 M $NaOCH_3$ in MeOH (14.8 mL, 7.4 mmol). The reaction was monitored and after 20 minutes, additional 0.5M $NaOCH_3$ in MeOH (7.4 mL) was added. After 10 minutes, the mixture was acidified with 6N HCl (2.0 mL) and concentrated. The product was purified by preparative HPLC to yield the title compound as a white solid TFA salt (1.0 g). MS m/z: [M+H$^+$] calcd for $C_{29}H_{36}FN_3O_4S$, 542.24; found 542.6.

Example 5

4'-(2-Ethoxy-4-ethyl-5-{[(S)-2-(2-methoxycarbonylethylsulfanyl)-4-methylpentanoylamino]methyl}imidazol-1-ylmethyl)-3'-fluorobiphenyl-2-carboxylic Acid

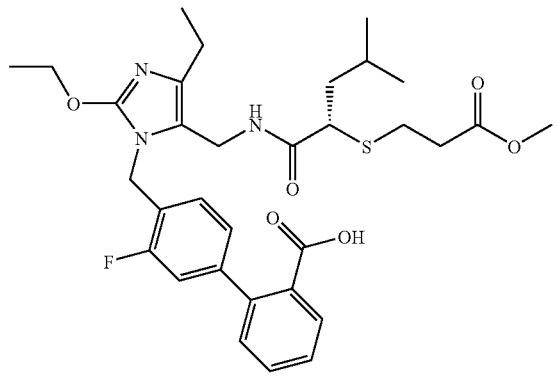

4'-{2-Ethoxy-4-ethyl-5-[((S)-2-mercapto-4-methylpentanoylamino)methyl]-imidazol-1-ylmethyl}-3'-fluorobiphenyl-2-carboxylic acid (90 mg, 0.2 mmol) in MeCN (5 mL) was added to a nitrogen-purged cold, aqueous saturated solution of $NaHCO_3$ (5 mL) in an ice bath, and immediately followed by the addition of methyl acrylate (77 μL). The mixture was stirred for 5 minutes. Concentrated HCl was then added dropwise until the pH reached ~3-4. The mixture was extracted with EtOAc, and the organic layer was dried over $MgSO_4$. Evaporation of the organic layer afforded the title compound as a white foam (85 mg, 96% purity) TFA salt. MS m/z: [M+H$^+$] calcd for $C_{32}H_{40}FN_3O_6S$, 614.26; found 614.0.

LC/MS/MS Equipment and Conditions for Quantitation

Sciex API 4000 or 5000 with turbo-ESI source interfaced with a Shimadzu LC-20AD HPLC was used for bioanalysis. Aliquots of 10 μL were injected onto the LC/MS/MS system. A Hypurity C18 column (50×2.1 mm, 3μ) was used to perform the chromatographic separation. The mobile phase consisted of (A) water with 0.2% formic acid; and (B) MeCN with 0.2% formic acid with a flow rate of 0.5 mL/min.

The LC gradient was run from 15% B to 70% B in 3.0 min, 70% B to 95% B in 0.5 min, hold at 95% B for 0.7 min, 95% B to 15% B in 0.3 min and then stop. Detection was achieved by turbo-ESI mass spectrometry operated in a positive ion mode with MRM transitions at m/z 528.1/229.1 for I-a; m/z 614.2/229.1 for III-a; m/z 600.2/229.1 for IV-a; and m/z 605.3/201.2 for the internal standard.

Example 6

Monomer Detection Method for 4'-{2-ethoxy-4-ethyl-5-[((S)-2-mercapto-4-methylpentanoylamino)methyl]-imidazol-1-ylmethyl}-3'-fluorobiphenyl-2-carboxylic Acid (compound I-a)

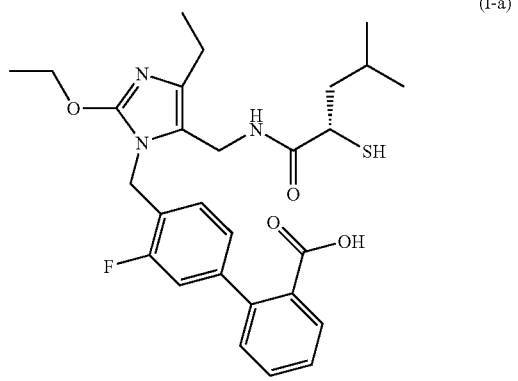

(I-a)

In Vivo Blood Sample Collection Procedure

Rat blood (0.3 mL) was placed into EDTA microtainer tubes containing methyl acrylate (3 μL) (1:100 volume ratio of methyl acrylate:blood). Blood and methyl acrylate were mixed by gentle rolling and tapping of the tube. After 30 minutes of reaction at room temperature, the blood samples were placed on ice until centrifugation. The blood was processed to obtain plasma by centrifugation for 4 minutes at approximately 12,000 rpm. 0.15 mL of plasma was then transferred to cluster tubes on dry ice.

Procedure for Preparation of Calibration Standards and QC Samples

The calibration set consisted of thirteen concentrations, prepared by spiking the specified amount of 4'-2-ethoxy-4-ethyl-5-{[(S)-2-(2-methoxycarbonylethylsulfanyl)-4-methylpentanoylamino]methyl}imidazol-1-ylmethyl)-3'-fluorobiphenyl-2-carboxylic acid (compound III-a):

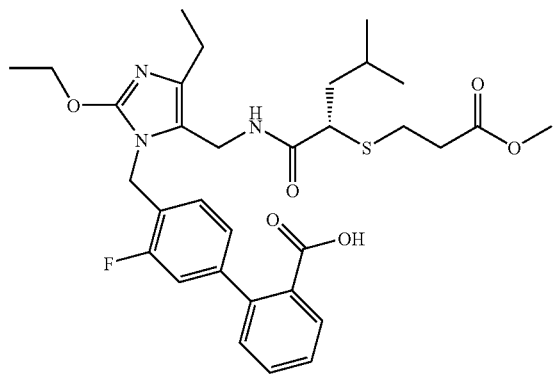

(III-a)

into a specified volume of blank rat plasma containing 1% (v/v) of methyl acrylate. Compound III-a is the methyl acrylate derivative of compound I-a. In general, the calibration curve range was 0.1 to 1000 ng/mL of compound III-a in rat plasma. The highest concentration standard was prepared by diluting 10 μL of 0.1 mg/mL stock solution to 990 μL of 1% methyl acrylate containing blank plasma. The rest of the standards were prepared from the highest concentration standard through serial dilutions with blank plasma containing 1% methyl acrylate. Five levels of QCs were prepared in the methyl acrylate containing blank plasma in the same manner as calibration standards.

Subsequent studies were conducted using dog and monkey plasma. Accordingly, similar calibration standards were prepared in dog and monkey plasma.

Procedure for Biological Sample Extraction and Reconstitution

Plasma samples were extracted by protein precipitation. In general, 200 μL of MeCN containing a specified concentration of the internal standard was added into a 50 μL aliquot of each plasma calibration standard, QC, and in vivo plasma sample. The plasma samples were then vortexed and centrifuged. 100 μL of extract was then taken from each plasma sample and reconstituted into 200 μL of 5% MeCN/water containing 0.2% formic acid.

LC-MS/MS Analysis

Multiple reaction monitoring (MRM) is the standard technique for quantitative LC-MS/MS experiments. Four specific MRM transitions for compound I-a, compound III-a, compound IV-a, and the internal standard were simultaneously monitored by LC-MS/MS. 4'-(5-{[(5)-2-(2-Carboxyethylsulfanyl)-4-methylpentanoylamino]methyl}-2-ethoxy-4-ethylimidazol-1-ylmethyl)-3'-fluorobiphenyl-2-carboxylic acid (compound IV-a):

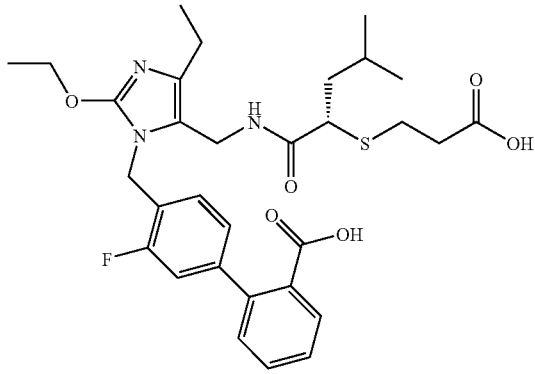

(IV-a)

is the hydrolyzed form of compound III-a. Compound III-a completely hydrolyzes to compound IV-a in rat plasma, but not in dog or monkey plasma. Therefore, the calibration curve was established by plotting the peak area ratio of compound IV-a/internal standard (for rat plasma) or compound III-a/internal standard (for dog and monkey plasma) versus the concentration of each calibration standard. The relevant derivative concentrations of in vivo samples were determined from the calibration curve. The monomer concentration (in ng/mL units) was calculated from the concentration of the relevant derivative multiplied by the correction factor of the ratio of the molecular weight of the monomer/molecular weight of the derivative.

FIG. 1 shows a representative ion chromatogram for the monomer detection method in rat plasma, showing a predominant ion peak of MRM (m/z) 600.2/229.1 at a retention time of 2.38 minutes for compound IV-a.

Figure 2:
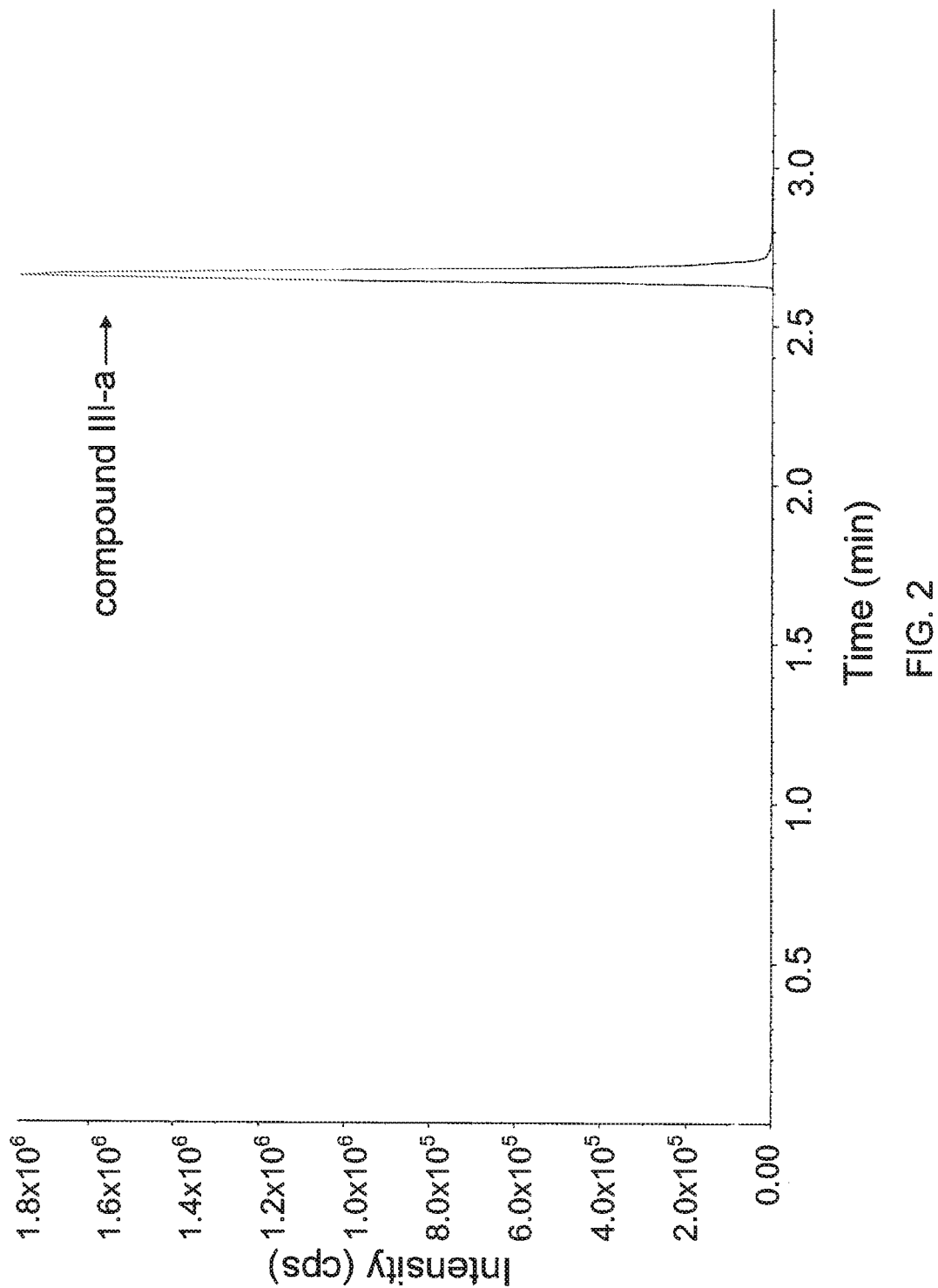
FIG. 2 shows a representative ion chromatogram for the monomer detection method in dog plasma, showing a predominant ion peak of MRM (m/z) 614.2/229.1 at a retention time of 2.65 minutes for compound III-a.

FIG. 2 shows a representative ion chromatogram for the monomer detection method in dog plasma, showing a predominant ion peak of MRM (m/z) 614.2/229.1 at a retention time of 2.65 minutes for compound III-a.

Figure 3:
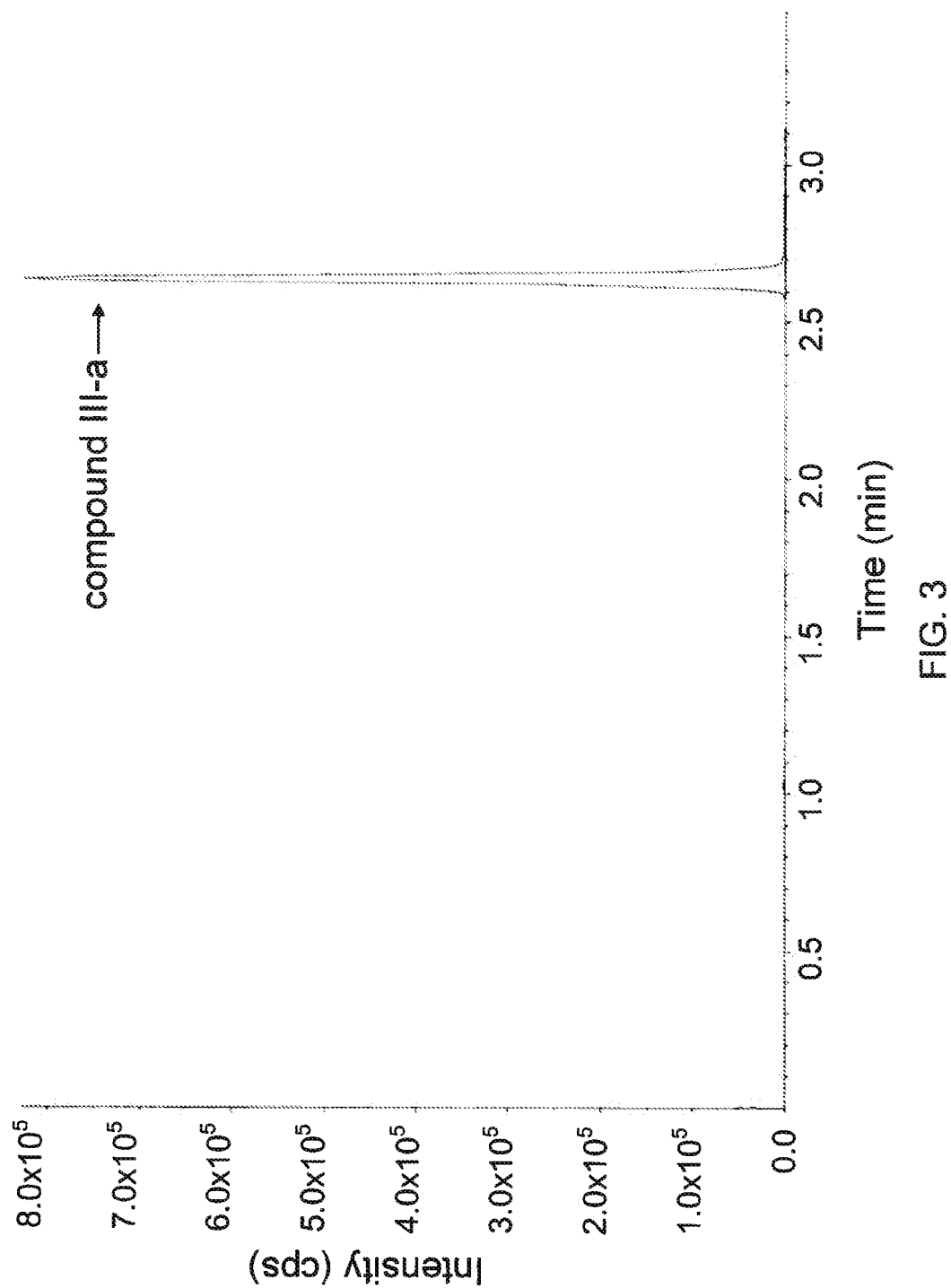
FIG. 3 shows a representative ion chromatogram for the monomer detection method in monkey plasma, showing a predominant ion peak of MRM (m/z) 614.2/229.1 at a retention time of 2.65 minutes for compound III-a.

FIG. 3 shows a representative ion chromatogram for the monomer detection method in monkey plasma, showing a predominant ion peak of MRM (m/z) 614.2/229.1 at a retention time of 2.65 minutes for compound III-a.

Example 7

Total Reducible Monomer Detection Method for 4'-{2-ethoxy-4-ethyl-5-[((S)-2-mercapto-4-methyl-pentanoylamino)methyl]-imidazol-1-ylmethyl}-3'-fluorobiphenyl-2-carboxylic Acid (compound I-a)

In Vivo Blood Sample Collection Procedure 0.3 mL of blood collected from the rats at each time point, was placed into EDTA microtainer tubes containing 5 µL of 3 µM DTT. The final concentration of DTT in the blood was 50 mM. Blood and DTT were mixed by gentle rolling and tapping of the tube. After 20 minutes of incubation at room temperature, the blood samples were placed on ice until centrifugation. The blood was processed to obtain plasma by centrifugation for 4 minutes at approximately 12,000 rpm. 0.15 mL of plasma was then transferred to cluster tubes on dry ice.

Procedure for Preparation of Calibration Standards and QC Samples

The calibration set consisted of thirteen concentrations, prepared by spiking the specified amount of compound I-a into a specified volume of blank rat plasma containing 50 mM DTT. In general, the calibration curve range was 0.1 to 1000 ng/mL of compound I-a in rat plasma. The highest concentration standard was prepared by diluting 10 µL of 0.1 mg/mL stock solution to 990 µL of 50 mM DTT containing blank plasma. The rest of the standards were prepared from the highest concentration standard through serial dilutions with blank plasma containing DTT. Five levels of QCs were prepared in the DTT containing blank plasma in the same manner as calibration standards.

Subsequent studies were conducted using dog and monkey plasma. Accordingly, similar calibration standards were prepared in dog and monkey plasma.

Procedure for Biological Sample Extraction and Reconstitution

Plasma samples were extracted by protein precipitation. In general, 200 µL of MeCN containing a specified concentration of the internal standard was added into a 50 µL aliquot of each plasma calibration standard, QC, and in vivo plasma sample. The plasma samples were then vortexed and centrifuged. 100 µL of extract was then taken from each plasma sample and reconstituted into 200 µL of 5% MeCN/water containing 0.2% formic acid and 20 mM TCEP.

LC-MS/MS Analysis

Two specific MRM transitions for compound I-a and the internal standard were simultaneously monitored by LC-MS/MS. The calibration curve was established by plotting the peak area ratio of compound I-a/internal standard versus the concentration of each calibration standard. The total reducible compound I-a concentrations of in vivo samples were determined from the calibration curve.

Figure 4:
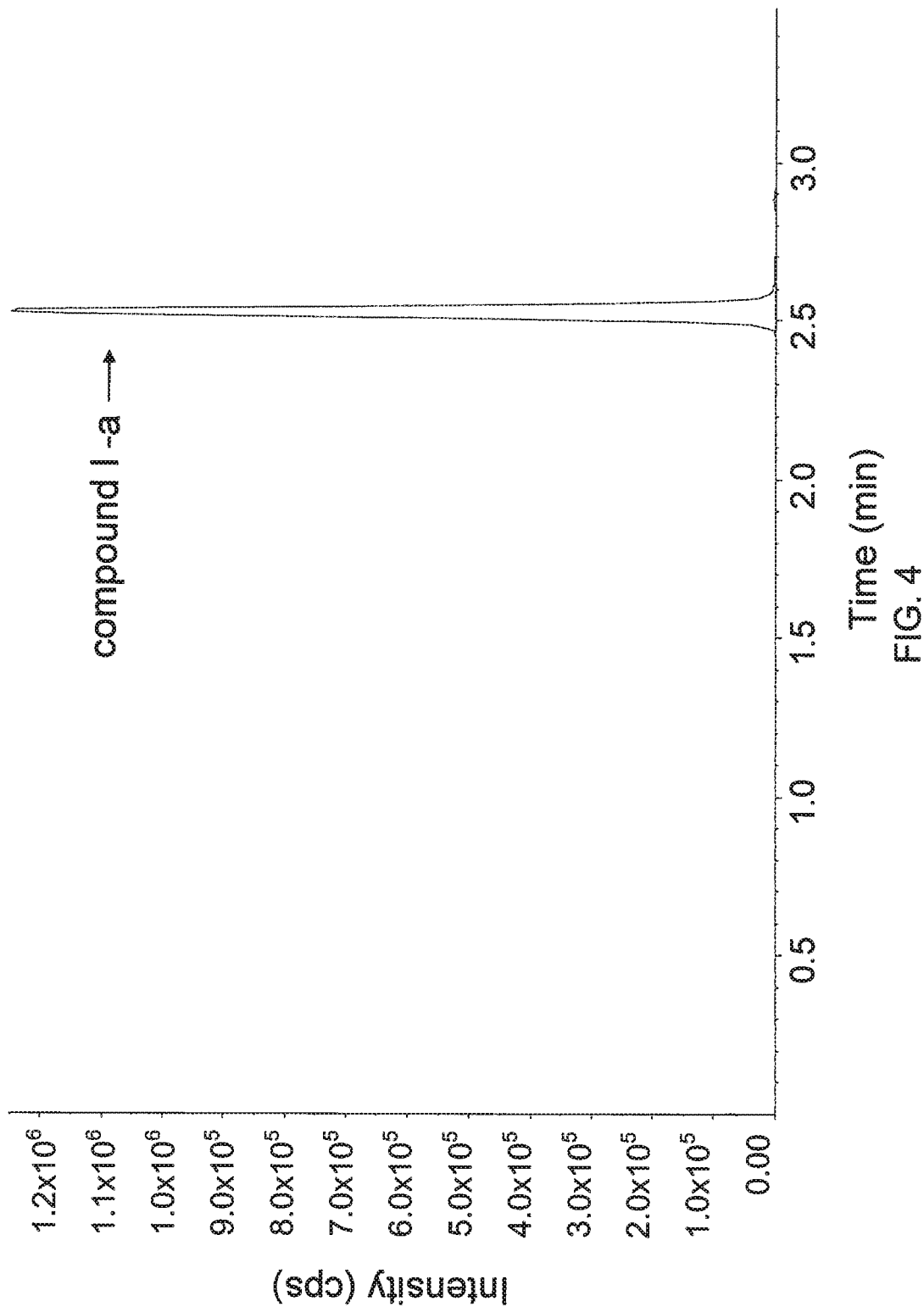
FIG. 4 shows a representative ion chromatogram for the total reducible monomer detection method in rat plasma showing a predominant ion peak of MRM (m/z) 528.2/229.1 at a retention time 2.52 minutes for compound I-a.

FIG. 4 shows a representative ion chromatogram for the total reducible monomer detection method in rat plasma showing a predominant ion peak of MRM (m/z) 528.2/229.1 at a retention time 2.52 minutes for compound I-a.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A compound of formula II:

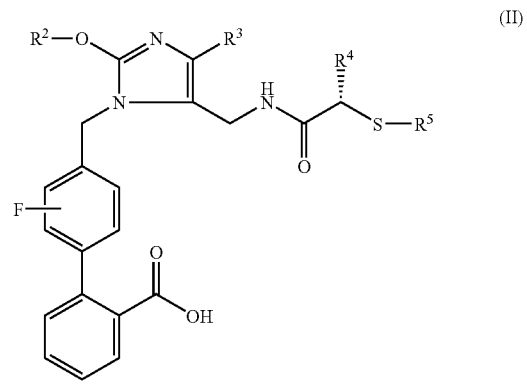

wherein: $R^2$ is —$C_{1-10}$alkyl; $R^3$ is —$C_{1-6}$alkyl or —$C_{3-6}$cycloalkyl; $R^4$ is —$C_{1-6}$alkyl; and $R^5$ is —$CH_2CH_2C(O)$O—$C_{1-6}$alkyl or —$CH_2CH_2C(O)OH$; or a salt thereof.

2. The compound of claim 1, wherein $R^2$ is —$CH_2CH_3$ or —$(CH_2)_2CH_3$.

3. The compound of claim 1, wherein $R^3$ is —$CH_2CH_3$ or cyclopropyl.

4. The compound of claim 1, wherein $R^4$ is —$CH_2CH(CH_3)_2$.

5. The compound of claim 1, whereín $R^5$ is —$CH_2CH_2C(O)O$—$CH_3$ or —$CH_2CH_2C(O)OH$.

* * * * *